US010734587B2

(12) United States Patent
Parham et al.

(10) Patent No.: US 10,734,587 B2
(45) Date of Patent: Aug. 4, 2020

(54) FORMULATIONS OF LUMINESCENT COMPOUNDS

(71) Applicant: Merck Patent GmbH, Darmstadt (DE)

(72) Inventors: Amir Hossain Parham, Frankfurt am Main (DE); Philipp Stoessel, Frankfurt am Main (DE); Christof Pflumm, Darmstadt (DE); Anja Jatsch, Frankfurt am Main (DE); Joachim Kaiser, Darmstadt (DE); Anna Hayer, Mainz (DE)

(73) Assignee: Merck Patent GmbH (DE)

( * ) Notice: Subject to any disclaimer, the term of this patent is extended or adjusted under 35 U.S.C. 154(b) by 396 days.

(21) Appl. No.: 15/125,215

(22) PCT Filed: Feb. 9, 2015

(86) PCT No.: PCT/EP2015/000377

§ 371 (c)(1),
(2) Date: Sep. 12, 2016

(87) PCT Pub. No.: WO2015/135625

PCT Pub. Date: Sep. 17, 2015

(65) Prior Publication Data

US 2017/0084844 A1 Mar. 23, 2017

(30) Foreign Application Priority Data

Mar. 13, 2014 (EP) .................................... 14000920

(51) Int. Cl.

| | |
|---|---|
| ***H01L 51/00*** | (2006.01) |
| ***C09K 11/06*** | (2006.01) |
| ***H01L 51/50*** | (2006.01) |
| ***H01J 9/22*** | (2006.01) |
| ***C07D 209/82*** | (2006.01) |
| ***C07D 413/10*** | (2006.01) |
| ***C07D 403/14*** | (2006.01) |
| ***C07D 403/10*** | (2006.01) |

(Continued)

(52) U.S. Cl.

CPC ........ *H01L 51/0067* (2013.01); *C07D 209/82* (2013.01); *C07D 221/20* (2013.01); *C07D 251/24* (2013.01); *C07D 403/04* (2013.01); *C07D 403/10* (2013.01); *C07D 403/14* (2013.01); *C07D 413/10* (2013.01); *C07D 413/14* (2013.01); *C09D 5/22* (2013.01); *C09D 5/24* (2013.01); *C09K 11/025* (2013.01); *C09K 11/06* (2013.01); *H01J 9/223* (2013.01); *H01L 51/0039* (2013.01); *H01L 51/0043* (2013.01); *H01L 51/0052* (2013.01); *H01L 51/0072* (2013.01); *H01L 51/5004* (2013.01); *H01L 51/5012* (2013.01); *C09K 2211/1007* (2013.01); *C09K 2211/1011* (2013.01); *C09K 2211/1014* (2013.01); *C09K 2211/1029* (2013.01); *C09K 2211/1033* (2013.01); *C09K 2211/1044* (2013.01); *C09K 2211/1048* (2013.01); *C09K 2211/1059* (2013.01); *C09K 2211/1092* (2013.01); *C09K 2211/185* (2013.01); *H01L 51/001* (2013.01); *H01L 51/0007* (2013.01); *H01L 51/0085* (2013.01); *H01L 51/5016* (2013.01); *H01L 51/5056* (2013.01); *H01L 51/5072* (2013.01); *H01L 51/56* (2013.01); *H01L 2251/5384* (2013.01); *H01L 2251/55* (2013.01); *H01L 2251/552* (2013.01); *H01L 2251/556* (2013.01)

(58) Field of Classification Search

CPC . H01L 51/00; H01L 51/0072; H01L 51/0007; H01L 51/0085; H01L 51/56; H01L 51/001; H01L 51/5072; H01L 51/5056; H01L 51/5004; H01L 51/5012; H01L 51/0067; H01L 51/0052; H01L 51/0043; H01L 51/0039; H01L 2251/5384; H01L 2251/55; H01L 2251/552; H01L 2251/556; H01L 51/5016; C07D 209/82; C07D 413/14; C07D 221/20; C07D 403/04; C07D 403/10; C07D 403/14; C07D 413/10; C07D 251/24; H01J 9/223; C09D 5/24; C09D 5/22; C09K 2211/1011; C09K 2211/1014; C09K 2211/1033; C09K 2211/1044; C09K 2211/1048; C09K 2211/1059; C09K 2211/1092; C09K 2211/185; C09K 2211/1029; C09K 2211/1007; C09K 11/06; C09K 11/025

USPC ........................................... 428/690; 252/500

See application file for complete search history.

(56) References Cited

U.S. PATENT DOCUMENTS 7,294,849 B2 * 11/2007 Thompson .......... H01L 51/0085 257/40
7,868,331 B2 1/2011 Ono et al.

(Continued)

FOREIGN PATENT DOCUMENTS

JP 2013527989 A 7/2013
JP 2013539584 A 10/2013

(Continued)

OTHER PUBLICATIONS

CAS reg. No. 1411910-25-2, Dec. 5, 2012. (Year: 2012).*

(Continued)

*Primary Examiner* — Douglas J McGinty

(74) *Attorney, Agent, or Firm* — Faegre Drinker Biddle & Reath LLP

(57) ABSTRACT

The present invention relates to a formulation comprising organic materials for the production of organic electronic devices having a low failure rate.

13 Claims, No Drawings

(51) Int. Cl.

| | |
|---|---|
| ***C07D 413/14*** | (2006.01) |
| ***C07D 221/20*** | (2006.01) |
| ***C07D 251/24*** | (2006.01) |
| ***C07D 403/04*** | (2006.01) |
| ***C09D 5/22*** | (2006.01) |
| ***C09D 5/24*** | (2006.01) |
| ***C09K 11/02*** | (2006.01) |
| *H01L 51/56* | (2006.01) |

(56) References Cited

U.S. PATENT DOCUMENTS

| | | | | |
|---|---|---|---|---|
| 8,993,129 | B2 | 3/2015 | Endo et al. | |
| 8,994,013 | B2 | 3/2015 | Seo | |
| 9,076,976 | B2 | 7/2015 | Seo et al. | |
| 9,093,656 | B2 | 7/2015 | Pan et al. | |
| 9,099,658 | B2 | 8/2015 | Kawamura et al. | |
| 9,153,788 | B2 | 10/2015 | Adachi et al. | |
| 9,159,930 | B2 * | 10/2015 | Anemian | C09K 11/06 |
| 9,219,242 | B2 | 12/2015 | Ogiwara et al. | |
| 9,299,944 | B2 | 3/2016 | Seo et al. | |
| 9,660,199 | B2 * | 5/2017 | Shizu | C07D 401/10 |
| 10,069,079 | B2 * | 9/2018 | Stoessel | H01L 51/56 |
| 10,164,206 | B2 | 12/2018 | Seo et al. | |
| 2012/0248968 | A1 | 10/2012 | Ogiwara et al. | |
| 2013/0306945 | A1 | 11/2013 | Seo | |
| 2015/0041784 | A1 | 2/2015 | Shizu et al. | |
| 2015/0105564 | A1 | 4/2015 | Adachi et al. | |
| 2015/0340623 | A1 * | 11/2015 | Kawamura | C07D 219/06 257/40 |
| 2016/0035992 | A1 * | 2/2016 | Stoessel | H01L 51/5012 257/40 |
| 2016/0093812 | A1 * | 3/2016 | Stoessel | C09K 11/06 257/40 |
| 2016/0181545 | A1 * | 6/2016 | Stoessel | C09K 11/06 257/40 |
| 2016/0315268 | A1 * | 10/2016 | Stoessel | H01L 51/0067 |
| 2017/0077418 | A1 * | 3/2017 | Stoessel | H01L 51/0054 |
| 2017/0092875 | A1 * | 3/2017 | Parham | H01L 51/0052 |
| 2017/0256720 | A1 | 9/2017 | Adachi et al. | |

FOREIGN PATENT DOCUMENTS

| | | | | |
|---|---|---|---|---|
| JP | 2013236058 | A | 11/2013 | |
| JP | 2013239431 | A | 11/2013 | |
| JP | 5366106 | B1 | 12/2013 | |
| JP | 2013258402 | A | 12/2013 | |
| KR | 20130099814 | A | 9/2013 | |
| KR | 20150008859 | A | 1/2015 | |
| TW | 201350558 | A | 12/2013 | |
| WO | WO-2004112440 | A1 | 12/2004 | |
| WO | WO-2011070963 | A1 | 6/2011 | |
| WO | WO-2011137922 | A1 * | 11/2011 | H01L 51/005 |
| WO | WO-2013081088 | A1 | 6/2013 | |
| WO | WO-2013154064 | A1 | 10/2013 | |
| WO | WO-2013157495 | A1 | 10/2013 | |
| WO | WO-2013172255 | A1 * | 11/2013 | C07D 401/10 |
| WO | WO-2013180241 | A1 | 12/2013 | |
| WO | WO-2014013947 | A1 | 1/2014 | |

OTHER PUBLICATIONS

International Search Report for PCT/EP2015/000360 dated Jun. 12, 2015.

International Search Report for PCT/EP2015/000377 dated May 7, 2015.

Ishimatsu, R., et al., “Solvent Effect on Thermally Activated Delayed Fluorescence by 1,2,3,5-Tetrakis(carbazol-9-yl)-4,6-dicyanobenzene”, Journal of Physical Chemistry A, vol. 117, No. 27, (2013), pp. 5607-5612.

Uoyama, H., et al., “Highly efficient organic light-emitting diodes from delayed fluorescence”, Nature, vol. 492, No. 7428, (2012), pp. 234-238.

Ziegler, J., et al., “Silica-Coated inP/ZnS Nanocrystals as Converter Material in White LEDs”, Advanced Materials, vol. 20, No. 21, (2008), pp. 4068-4073.

Li, Y., et al., “White organic light-emitting devices with CdSe/ZnS quantum dots as a red emitter”, Journal of Applied Physics, 2005, vol. 97, pp. 113501-113504.

* cited by examiner

FORMULATIONS OF LUMINESCENT COMPOUNDS

CROSS-REFERENCE TO RELATED APPLICATIONS

This application is a national stage application (under 35 U.S.C. § 371) of PCT/EP2015/000377, filed Feb. 9, 2015, which claims benefit of European Application No. 14000920.0, filed Mar. 13, 2014, both of which are incorporated herein by reference in their entirety.

The present invention relates to formulations comprising luminescent compounds having a small singlet-triplet separation, and to the use thereof for the production of organic electronic devices.

The structure of a specific organic electronic device in which organic semiconductors are employed as functional materials is disclosed, for example, in U.S. Pat. Nos. 4,539,507, 5,151,629, EP 0676461 and WO 98/27136. This is an organic light-emitting diode (OLED), a specific device from the group of organic electroluminescent devices. The emitting materials employed here are also, in particular, organometallic iridium and platinum complexes, which exhibit phosphorescence instead of fluorescence (M. A. Baldo et al., *Appl. Phys. Lett.* 1999, 75, 4-6). For quantum-mechanical reasons, an up to four-fold increase in the energy and power efficiency is possible using organometallic compounds as phosphorescence emitters.

In spite of the good results achieved with organometallic iridium and platinum complexes, these also have, however, a number of disadvantages: thus, iridium and platinum are rare and expensive metals. It would therefore be desirable, for resource conservation, to be able to avoid the use of these rare metals. Furthermore, metal complexes of this type in some cases have lower thermal stability than purely organic compounds, so that the use of purely organic compounds would also be advantageous for this reason so long as they result in comparably good efficiencies. Furthermore, blue-, in particular deep-blue-phosphorescent iridium and platinum emitters having high efficiency and a long lifetime can only be achieved with technical difficulty, so that there is also a need for improvement here. Furthermore, there is, in particular, a need for improvement in the lifetime of phosphorescent OLEDs comprising Ir or Pt emitters if the OLED is operated at elevated temperature, as is necessary for some applications. Furthermore, many of the known organic semiconductor materials for the production of electronic devices are applied by vapour deposition by means of sublimation in vacuo, which is in some cases very complex and expensive. In addition, not all materials can be applied by vapour deposition, meaning that certain organic materials cannot be used in electronic devices owing to their poor processability, in spite of good opto-electronic properties. In particular for the mass production of electronic products, inexpensive processability of organic materials is of very great commercial interest. Highly efficient organic molecules which can be processed from solution are therefore desirable.

An alternative to the development of phosphorescent metal complexes is the use of emitters which exhibit thermally activated delayed fluorescence (TADF) (for example H. Uoyama et al., Nature 2012, Vol. 492, 234). These are organic materials in which the energetic separation between the lowest triplet state $T_1$ and the first excited singlet state $S_1$ is so small that this energy separation is smaller or in the region of thermal energy. For quantum-statistical reasons, the excited states arise to the extent of 75% in the triplet state and to the extent of 25% in the singlet state on electronic excitation in the OLED. Since purely organic molecules usually cannot emit from the triplet state, 75% of the excited states cannot be utilised for emission, meaning that in principle only 25% of the excitation energy can be converted into light. However, if the energetic separation between the lowest triplet state and the lowest excited singlet state is not or is not significantly greater than the thermal energy, which is described by $k_BT$, where $k_B$ stands for the Boltzmann constant and T stands for the temperature, the first excited singlet state of the molecule is accessible from the triplet state through thermal excitation and can be occupied thermally. Since this singlet state is an emissive state from which fluorescence is possible, this state can be used for the generation of light. Thus, the conversion of up to 100% of electrical energy into light is in principle possible on use of purely organic materials as emitters. Thus, an external quantum efficiency of greater than 19% is described in the prior art, which is of the same order of magnitude as for phosphorescent OLEDs. It is thus possible, using purely organic materials of this type, to achieve very good efficiencies and at the same time to avoid the use of rare metals, such as iridium or platinum. Furthermore, it is also possible using such materials to achieve highly efficient blue-emitting OLEDs.

The compounds exhibiting TADF which are described in the prior art are all applied by vacuum vapour deposition by means of sublimation in order to produce electronic devices comprising these compounds.

In general, there is still a considerable need for improvement in the case of the compounds from the prior art, in particular with respect to processability. In particular, the failure rate in the production of organic electronic devices, such as OLEDs, is still too great, which adversely impacts the economic efficiency of the production processes.

The technical object on which the present invention is based thus consists in the provision of substance compositions which allow inexpensive production of organic electronic devices, in particular of OLEDs, where the devices have very good performance data and the failure rates in the production of the devices are improved.

Surprisingly, it has been found that the technical object is achieved by means of the formulations described in greater detail below. These formulations allow the production of organic electronic devices, in particular also OLEDs, which are processed from solution. The devices produced by means of the formulations according to the invention have very good performance data and exhibit a significantly reduced failure rate during the production process. The formulations according to the invention therefore overcome the disadvantages known in the prior art. The electronic devices can easily be processed from solution. The formulations are thus suitable for inexpensive and reliable mass production of electronic devices.

The present invention therefore relates to a formulation comprising at least one type of organic luminescent compound (TADF compound) and at least one organic solvent, characterised in that the TADF compound has a separation between the lowest triplet state $T_1$ and the first excited singlet state $S_1$ of less than or equal to 0.15 eV.

Formulation in the present application is taken to mean a composition which, besides the at least one TADF molecule, also comprises an organic solvent or organic solvent mixture. The solvent or solvent mixture here is preferably present in excess.

Solvent mixture in the present application is taken to mean a mixture of at least two different solvents.

It is furthermore preferred for the formulation to be in liquid form. The formulation here can be a true solution, an emulsion, miniemulsion, dispersion or suspension, where it is very preferred for the formulation to be a true solution.

As shown elsewhere in the present invention, the formulation is used for the production of a layer of organic electronic devices, in particular the emission layer of OLEDs. During the production of the layer, the solvent or solvent mixture is removed, so that the TADF compound is present in the layer in excess with respect to the remaining solvent or solvent mixture. The solvent or solvent mixture is preferably only present in traces, if at all, in the layer of the organic electronic device. It is very preferred for the solvent or solvent mixture to have been removed completely and therefore no longer to be found in the applied layer.

The TADF compound is a carbon-containing compound which contains no metals. In particular, the TADF compound is an organic compound which is built up from the elements C, H, D, B, Si, N, P, O, S, F, Cl, Br and I.

The TADF compound preferably has a separation between $S_1$ and $T_1$ of less than or equal to 0.12 eV, particularly preferably less than or equal to 0.10 eV, very particularly preferably less than or equal to 0.08 eV and especially preferably less than or equal to 0.05 eV.

In a preferred embodiment, the $S_1$ level of the TADF compound has a higher energy than the $T_1$ level. The separation of the energy levels $S_1$ and $T_1$ is then defined as follows: $\Delta E=E(S_1)-E(T_1)$, where $\Delta E$ is less than or equal to 0.15 eV, preferably less than or equal to 0.12 eV, particularly preferably less than or equal to 0.10 eV, very particularly preferably less than or equal to 0.08 eV and especially preferably less than or equal to 0.05 eV.

A luminescent compound in the sense of the present invention is taken to mean a compound which is capable of emitting light at room temperature on optical excitation in an environment as is present in the organic electroluminescent device. The compound preferably has a luminescence quantum efficiency of at least 40%, particularly preferably at least 50%, very particularly preferably at least 60% and especially preferably at least 70%. The luminescence quantum efficiency is determined here in a layer in a mixture with the matrix material, as is to be employed in the organic electroluminescent device. The way in which the determination of the luminescence quantum yield is carried out for the purposes of the present invention is described in detail in general terms in the example part.

It is furthermore preferred for the TADF compound to have a short decay time. The decay time is preferably less than or equal to 50 μs. The way in which the decay time is determined for the purposes of the present invention is described in detail in general terms in the example part.

The energy of the lowest excited singlet state ($S_1$) and of the lowest triplet state ($T_1$) is determined by quantum-chemical calculation. The way in which this determination is carried out in the sense of the present invention is generally described in detail in the example part.

The TADF compound is preferably an aromatic compound which has both donor and also acceptor substituents, where the LUMO and the HOMO of the compound preferably only exhibit weak spatial overlap.

The TADF compound preferably has a small spatial overlap $\Lambda$ of the molecular orbitals which are involved in certain electronic transitions (charge-transfer states).

A small overlap of the molecular orbitals in the present application means that the value of the parameter $\Lambda$ is 0.3 or less, preferably 0.2 or less, very preferably 0.15 or less, very particularly preferably 0.1 or less and especially preferably 0.05 or less. The way in which the determination of the parameter $\Lambda$ is carried out in the sense of the present invention is described in detail in general terms in the example part.

What is meant by donor or acceptor substituents is adequately known to the person skilled in the art. Suitable donor substituents are, in particular, diaryl- and diheteroarylamino groups and carbazole groups or carbazole derivatives, each of which are preferably bonded to the aromatic compound via N. These groups may also be substituted further. Suitable acceptor substituents are, in particular, cyano groups, but also, for example, electron-deficient heteroaryl groups, which may also be substituted further.

The acceptor group A (also called acceptor substituent) in the present application is taken to mean a group which is an electron-acceptor group. It is well known to the person skilled in the art what is understood under an acceptor group. It is preferred for the acceptor group to have a negative inductive effect (−I) and/or a negative mesomeric effect (−M). The determination of the parameters with the aid of the Hammett equation is also well known to the person skilled in the art. Suitable acceptor substituents are, in particular, cyano groups, but also $CF_3$ and, for example, electron-deficient heteroaryl groups, which may also be further substituted. Examples of preferred electron-deficient heteroaryl groups are selected from the group consisting of triazines, pyrimidines, phosphine oxides and ketones.

The donor group D (also called donor substituent) in the present application is taken to mean a group which is an electron-donor group. It is well known to the person skilled in the art what is understood under a donor group. It is preferred for the donor group to have a positive inductive effect (+I) and/or a positive mesomeric effect (+M). The determination of the parameters with the aid of the Hammett equation is well known to the person skilled in the art. Suitable donor substituents are, in particular, diaryl- or diheteroarylamino groups and carbazole groups or carbazole derivatives, such as indenocarbazoles or indolocarbazoles, each of which is preferably bonded to the bridge V or to the group A via N. These groups may also be further substituted.

Examples of suitable molecules which exhibit TADF are the structures shown in the following overview.

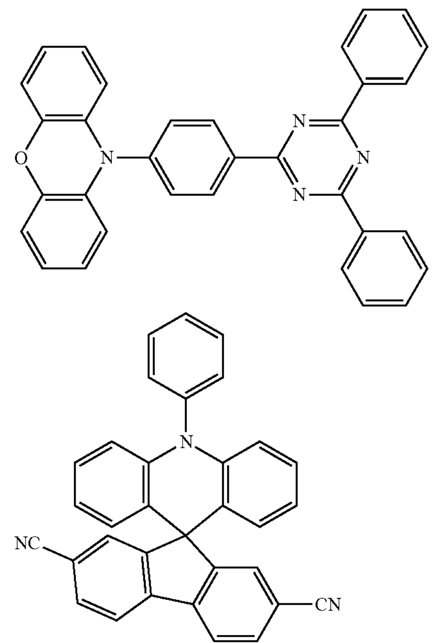

-continued
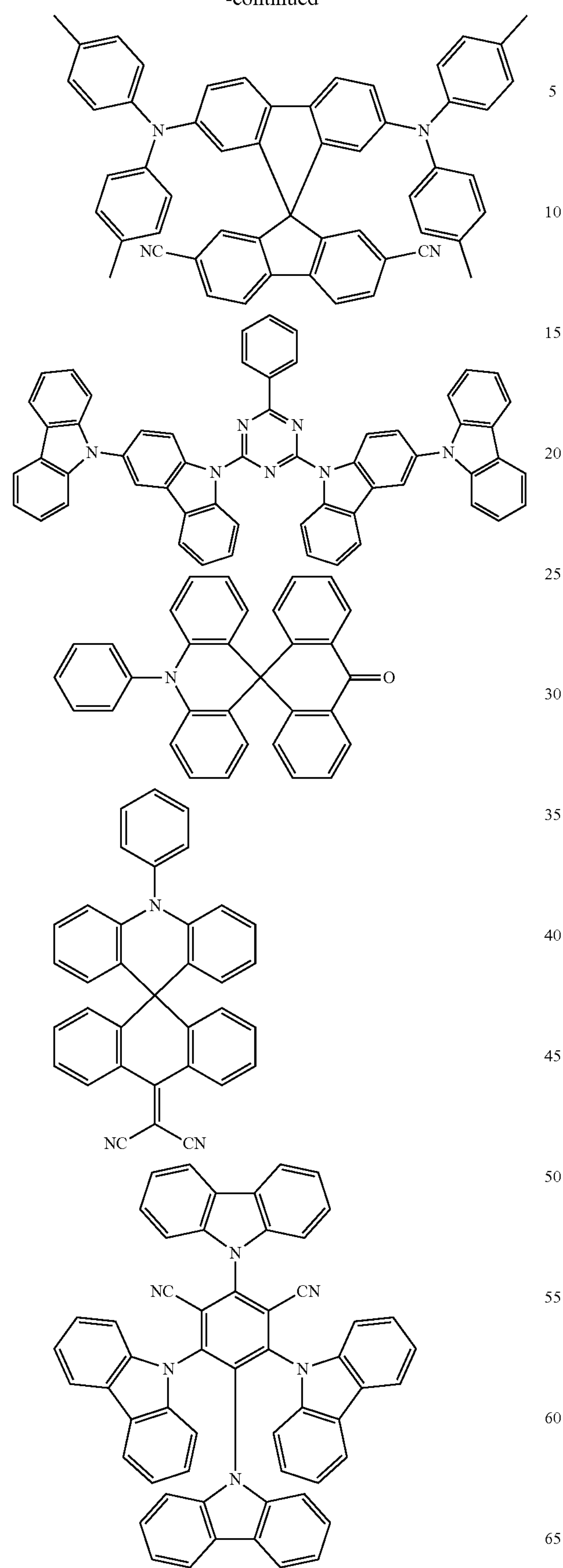
-continued
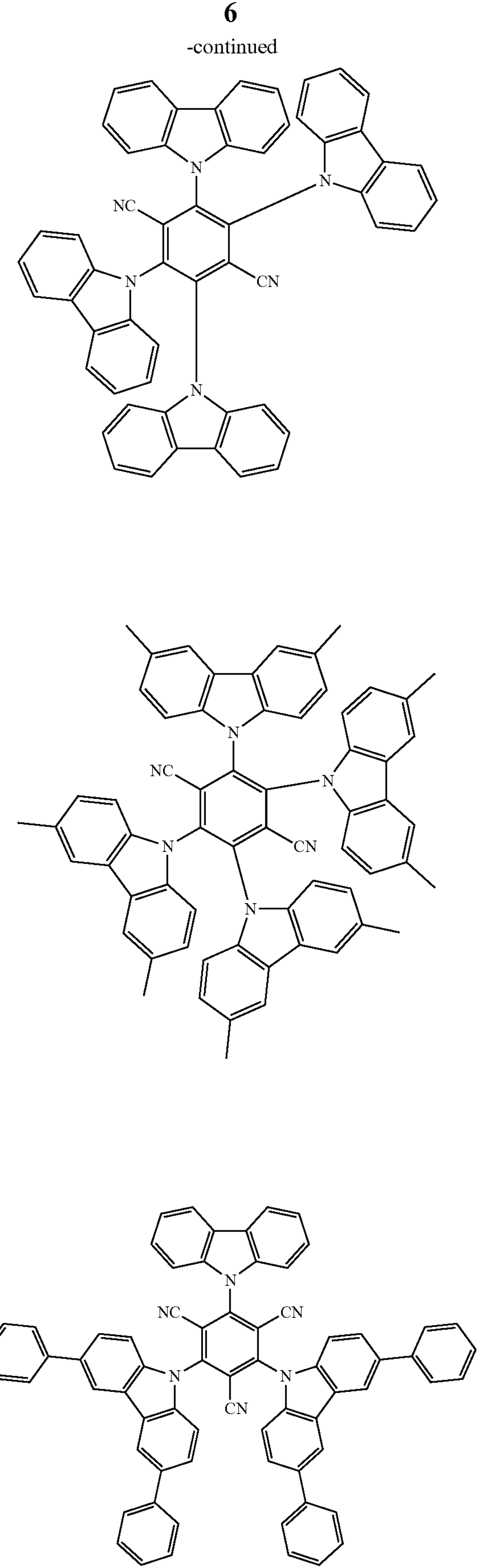

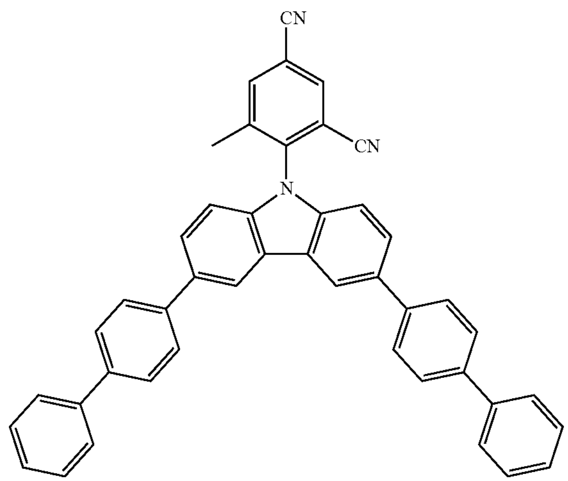
CN
CN
N
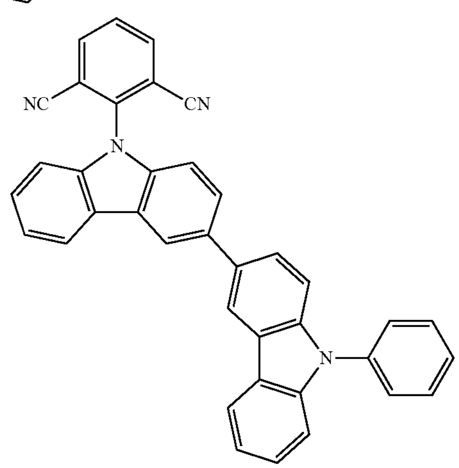
NC
CN
N
N
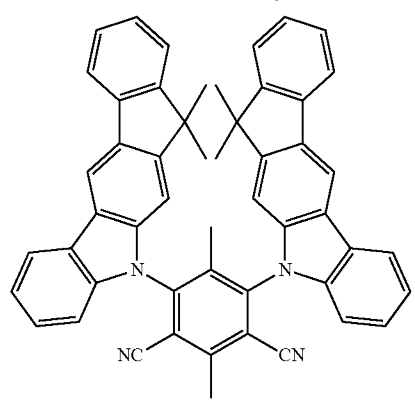
N
N
NC
CN
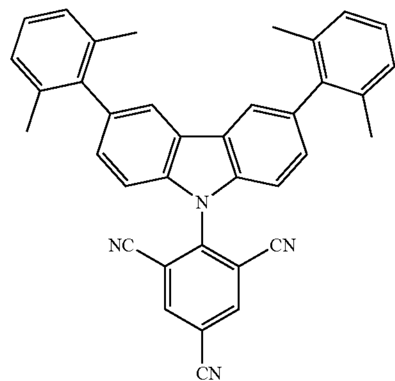
N
NC
CN
CN
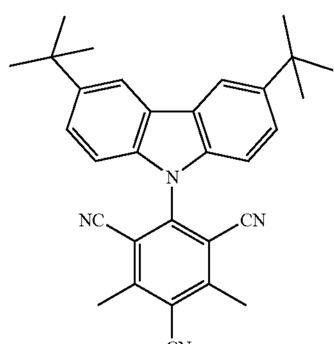
N
NC
CN
CN
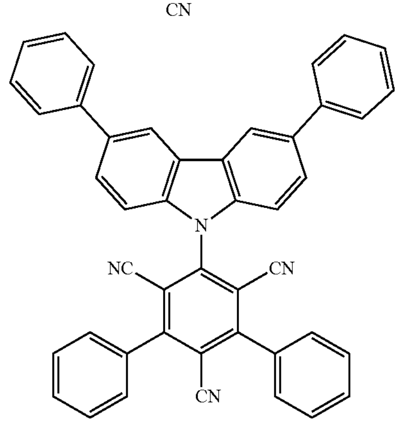
N
NC
CN
CN
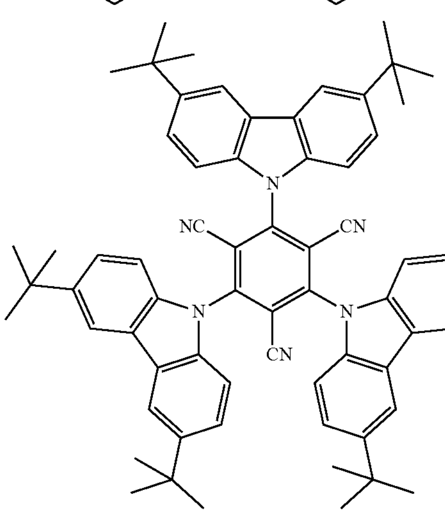
N
NC
CN
N
CN
N
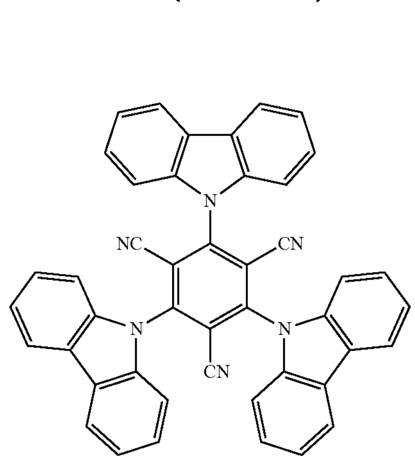
N
NC
CN
N
CN
N -continued

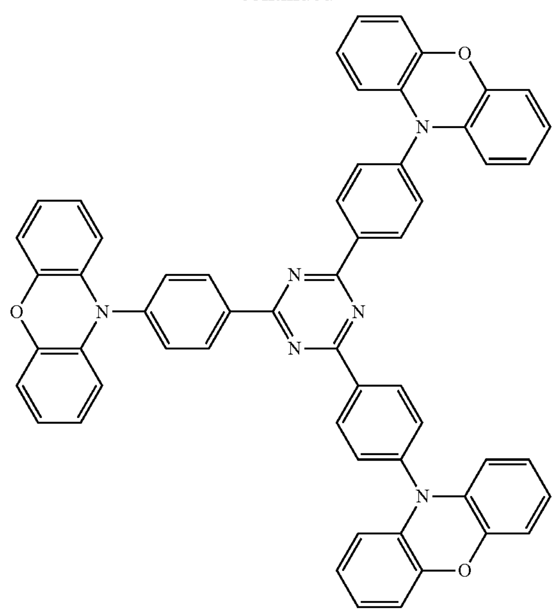

-continued

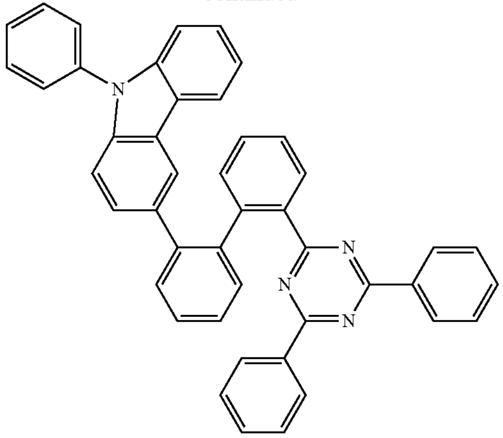

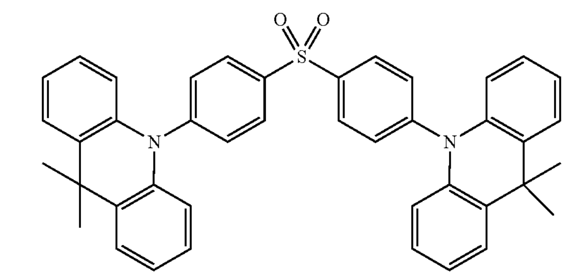

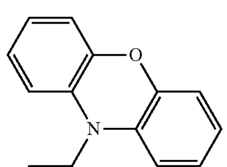

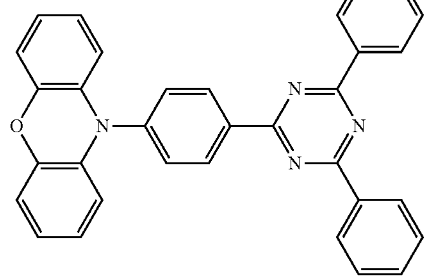

A multiplicity of TADF compounds are known in the prior art, and the person skilled in the art is presented with absolutely no difficulties in selecting the TADF compounds from the prior art (for example: Tanaka et al., Chemistry of Materials 25(18), 3766 (2013), Zhang et al., Nature Photonics advance online publication, 1 (2014), doi: 10.1038/nphoton.2014.12, Serevicius et al., Physical Chemistry Chemical Physics 15(38), 15850 (2013), Youn Lee et al., Applied Physics Letters 101(9), 093306 (2012), Nasu et al., ChemComm, 49, 10385 (2013), WO 2013/154064, WO 2013/161437, WO 2013/081088, WO 2013/011954).

The TADF compound is therefore preferably an aromatic compound which contains both donor and acceptor substituents.

The solvent used or the solvents (in the case of a solvent mixture) preferably have a surface tension of at least 28 mN/m, preferably at least 30 mN/m, very preferably at least 32 mN/m and very particularly preferably at least 35 mN/m.

Furthermore, the boiling or sublimation point of the solvent or solvents is preferably less than 300° C. and preferably less than 260° C.

The viscosity of the solvent or of the various solvents of a solvent mixture is very preferably greater than 3 mPa*s and preferably greater than 5 mPa*s.

Furthermore, the molecular weight of the solvent or solvents is preferably less than or equal to 1000 g/mol, preferably less than or equal to 700 g/mol, very preferably less than or equal to 500 g/mol and particularly preferably less than or equal to 300 g/mol.

As already explained, the solvent or the solvents of a solvent mixture is (are) present in the formulation in excess compared with the TADF compound. The concentration of the TADF compound in the formulation, based on the entire formulation, is preferably in the range from 1 to 20% by weight, very preferably in the range from 3 to 15% by weight and particularly preferably in the range from 5 to 12% by weight.

The person skilled in the art will be able to select from a multiplicity of solvents and solvent mixtures in order to prepare the formulations according to the invention.

Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The formulation of the present invention may preferably comprise 0.01 to 20% by weight, very preferably 0.05 to 10% by weight, particularly preferably 0.1 to 5% by weight and especially preferably 0.5 to 5% by weight of low-molecular-weight organic semiconductor materials, where low-molecular-weight organic semiconductor materials (for example TADF compound, matrix materials, emitters, hole-transport and electron-transport materials, hole- and electron-blocking materials) are taken to mean those which have a molecular weight of less than or equal to 2000 g/mol, preferably less than or equal to 1500 g/mol, very preferably less than or equal to 1000 g/mol, very particularly preferably less than or equal to 700 g/mol and especially preferably less than or equal to 600 g/mol.

The formulation of the present invention comprises one or more organic solvents, preferably at least one aromatic solvent. The solvents are preferably selected from the group consisting of aromatic hydrocarbons, such as toluene, o-, m- or p-xylene, phenoxytoluenes, trimethylbenzenes (for example 1,2,3-, 1,2,4- and 1,3,5-trimethylbenzenes), tetralin, other mono-, di-, tri- and tetraalkylbenzenes (for example diethylbenzenes, methyl-cumene, tetramethylbenzenes etc), aromatic ethers (for example anisole, alkylanisoles, for example 2-, 3- and 4-isomers of methylanisole, 2,3-, 2,4-, 2,5-, 2,6-, 3,4- and 3,5-isomers of dimethylanisole), naphthalene derivatives, alkylnaphthalene derivatives (for example 1- and 2-methylnaphthalene), di- and tetrahydronaphthalene derivatives. Preference is likewise given to aromatic esters (for example alkyl benzoates), aromatic ketones (for example acetophenone, propiophenone), alkyl ketones (for example cyclohexanone), heteroaromatic solvents (for example thiophene, mono-, di- and trialkylthiophenes, 2-alkylthiazoles, benzothiazoles etc, pyridines), haloarylenes and aniline derivatives. These solvents may contain halogen atoms.

Particular preference is given to: 3-fluoro-rifluoromethylbenzene, trifluoro-methylbenzene, dioxane, trifluoromethoxybenzene, 4-fluorobenzene trifluoride, 3-fluoropyridine, toluene, 2-fluorotoluene, 2-fluorobenzene trifluoride, 3-fluorotoluene, pyridine, 4-fluorotoluene, 2,5-difluorotoluene, 1-chloro-2,4-difluorobenzene, 2-fluoropyridine, 3-chlorofluorobenzene, 1-chloro-2,5-difluorobenzene, 4-chlorofluorobenzene, chlorobenzene, 2-chlorofluorobenzene, p-xylene, m-xylene, o-xylene, 2,6-lutidine, 2-fluoro-m-xylene, 3-fluoro-o-xylene, 2-chlorobenzene trifluoride, dimethylformamide, 2-chloro-6-fluorotoluene, 2-fluoroanisole, anisole, 2,3-dimethylpyrazine, bromobenzene, 4-fluoroanisole, 3-fluoroanisole, 3-trifluoromethylanisole, 2-methylanisole, phenetole, benzenedioxole, 4-methylanisole, 3-methylanisole, 4-fluoro-3-methylanisole, 1,2-dichlorobenzene, 2-fluorobenzonitrile, 4-fluoroveratrol, 2,6-dimethylanisole, aniline, 3-fluorobenzonitrile, 2,5-dimethylanisole, 3,4-dimethylanisole, 2,4-dimethylanisole, benzonitrile, 3,5-dimethylanisole, N,N-dimethylaniline, 1-fluoro-3,5-dimethoxybenzene, phenyl acetate, N-methylaniline, methyl benzoate, N-methylpyrrolidone, morpholine, 1,2-dihydronaphthalene, 1,2,3,4-tetrahydronaphthalene, o-tolunitrile, veratrol, ethyl benzoate, N,N-diethylaniline, propyl benzoate, 1-methylnaphthalene, butyl benzoate, 2-methylbiphenyl, 2-phenylpyridine or 2,2'-bitolyl.

Particular preference is given to aromatic hydrocarbons, in particular toluene, phenoxytoluene, dimethylbenzenes (xylenes), trimethylbenzenes, tetralin and methylnaphthalenes, aromatic ethers, in particular anisole, and aromatic esters, in particular methyl benzoate.

Especial preference is given to aromatic ethers, in particular anisole and derivates thereof, such as alkylanisoles, and aromatic esters, in particular methyl benzoate.

These solvents can be used as a mixture of two, three or more.

Preferred organic solvents can have Hansen solubility parameters $H_d$ in the range from 17.0 to 23.2 $MPa^{0.5}$, $H_p$ in the range from 0.2 to 12.5 $MPa^{0.5}$ and $H_h$ in the range from 0.9 to 14.2 $MPa^{0.5}$. Particularly preferred organic solvents have Hansen solubility parameters $H_d$ in the range from 18.5 to 21.0 $MPa^{0.5}$, $H_p$ in the range from 2.0 to 6.0 $MPa^{0.5}$ and $H_h$ in the range from 2.0 to 6.0 $MPa^{0.5}$.

TABLE 2

Hansen solubility parameters of useful solvents

| Solvent | $H_d$ [$MPa^{0.5}$] | $H_h$ [$MPa^{0.5}$] | $H_p$ [$MPa^{0.5}$] |
|---|---|---|---|
| 1,2,3,4-Tetrahydro-1-naphthol | 19.6 | 9.2 | 12.8 |
| 1,2,3,4-Tetrahydronaphthalene | 19.1 | 2.3 | 4.0 |
| 1,2,3,4-Tetramethylbenzene | 18.7 | 1.8 | 1.6 |
| 1,2,3,5-Tetramethylbenzene | 18.7 | 1.8 | 1.6 |
| 1,2,3-Trimethylbenzene | 19.0 | 2.9 | 1.6 |
| 1,2,4,5-Tetramethylbenzene | 18.7 | 1.8 | 1.6 |
| 1,2,4-Trichlorobenzene | 20.5 | 6.9 | 2.7 |
| 1,2,4-Trimethylbenzene | 19.0 | 2.9 | 1.6 |
| 1,2-Dihydronaphthalene | 20.1 | 5.5 | 4.9 |
| 1,2-Dimethylnaphthalene | 21.0 | 1.7 | 5.2 |
| 1,3,3-Trimethyl-2-methyleneindole | 17.9 | 1.0 | 3.0 |
| 1,3-Benzodioxole | 19.7 | 7.4 | 7.9 |
| 1,3-Diisopropylbenzene | 17.5 | 0.2 | 1.1 |
| 1,3-Dimethylnaphthalene | 21.0 | 1.7 | 5.2 |
| 1,4-Benzodioxane | 19.5 | 8.7 | 7.2 |
| 1,4-Diisopropylbenzene | 17.5 | 0.6 | 1.6 |
| 1,4-Dimethylnaphthalene | 21.0 | 1.7 | 5.2 |
| 1,5-Dimethyltetralin | 19.3 | 5.5 | 2.6 |
| 1-Benzothiophene | 19.7 | 12.3 | 6.3 |
| 1-Bromonaphthalene | 23.1 | 10.3 | 6.1 |
| 1-Chloromethylnaphthalene | 22.1 | 9.9 | 5.3 |
| 1-Ethylnaphthalene | 20.7 | 7.8 | 4.4 |
| 1-Methoxynaphthalene | 21.4 | 10.5 | 7.5 |
| 1-Methylnaphthalene | 21.7 | 8.4 | 4.5 |
| 1-Methylindane | 19.4 | 5.7 | 2.5 |
| 1-Methylindole | 19.2 | 8.1 | 10.2 |
| 2,3,3-Trimethoxyindolenine | 19.6 | 6.8 | 4.2 |
| 2,3-Benzofuran | 21.3 | 5.5 | 5.6 |
| 2,3-Dihydrobenzofuran | 19.9 | 9.5 | 6.6 |
| 2,3-Dimethylanisole | 18.9 | 4.6 | 4.5 |
| 2,4-Dimethylanisole | 18.9 | 4.6 | 4.5 |
| 2,5-Dimethylanisole | 18.9 | 4.6 | 4.5 |
| 2,6-Diisopropylnaphthalene | 18.3 | 3.5 | 2.2 |
| 2,6-Dimethylanisole | 18.9 | 4.6 | 4.5 |
| 2,6-Dimethylnaphthalene | 20.1 | 5.0 | 3.0 |
| 2-Bromo-3-bromomethyl)thiophene | 19.3 | 7.3 | 6.6 |
| 2-Bromomethylnaphthalene | 22.0 | 9.4 | 7.2 |
| 2-Bromonaphthalene | 23.1 | 10.3 | 6.1 |
| 2-Ethoxynaphthalene | 20.5 | 10.0 | 7.0 |
| 2-Ethylnaphthalene | 20.7 | 7.8 | 4.4 |
| 2-Isopropylanisole | 17.7 | 4.3 | 5.4 |
| 2-Methylquinoline | 20.0 | 7.8 | 4.0 |
| 2-Methylanisole | 18.3 | 5.1 | 6.2 |
| 2-Methylindole | 17.8 | 9.7 | 4.8 |
| 2-Phenoxyethanol | 18.7 | 8.5 | 13.0 |
| 3,4-Dimethylanisole | 18.9 | 4.6 | 4.5 |

TABLE 2-continued

Hansen solubility parameters of useful solvents

| Solvent | $H_d$ [MPa$^{0.5}$] | $H_h$ [MPa$^{0.5}$] | $H_p$ [MPa$^{0.5}$] |
|---|---|---|---|
| 3,5-Dimethylanisole | 18.9 | 4.6 | 4.5 |
| 3-Bromoquinoline | 21.4 | 8.7 | 5.1 |
| 3-Isopropylbiphenyl | 19.1 | 1.3 | 1.9 |
| 3-Methylanisole | 18.7 | 5.7 | 5.4 |
| 4-Benzylacetone | 18.3 | 8.8 | 5.0 |
| 4-Isopropylbiphenyl | 19.0 | 2.5 | 1.9 |
| 4-Methoxybenzyl alcohol | 19.0 | 8.5 | 13.3 |
| 4-Methylanisole | 18.6 | 5.9 | 7.2 |
| 4-Phenyl-2-butanone | 18.3 | 8.8 | 5.0 |
| 5,6,7,8-Tetrahydro-1-naphthol | 19.6 | 7.2 | 10.9 |
| 5,6,7,8-Tetrahydro-2-naphthol | 19.6 | 7.2 | 10.9 |
| 5,6,7,8-Tetrahydro-2-naphthylamine | 20.1 | 7.9 | 8.6 |
| 5,6.7,8-Tetrahydro-1-naphthylamine | 20.1 | 7.9 | 8.6 |
| 5-Decanolide | 17.1 | 7.8 | 3.8 |
| 5-Methoxyindane | 19.8 | 9.8 | 4.0 |
| 5-Methoxyindole | 17.4 | 12.3 | 7.8 |
| 5-tert-Butyl-m-xylene | 17.6 | 3.4 | 2.2 |
| 6-Methoxy-1,2,3,4-tetrahydronapthalene | 19.4 | 6.8 | 5.4 |
| 6-Methylquinoline | 21.7 | 8.4 | 4.5 |
| 8-Methylquinoline | 21.7 | 8.4 | 4.5 |
| Acetophenone | 18.8 | 10.8 | 5.5 |
| Anisole | 18.5 | 5.5 | 5.2 |
| α-Pinene | 17.4 | 3.0 | 3.2 |
| Benzonitrile | 19.2 | 11.9 | 4.7 |
| Benzothiazole | 21.3 | 5.5 | 5.6 |
| Benzyl acetate | 18.2 | 7.3 | 6.4 |
| Benzyl alcohol | 19.1 | 6.7 | 14.2 |
| Bromobenzene | 19.8 | 7.6 | 4.3 |
| Butylbenzene | 17.6 | 2.6 | 1.7 |
| Butyl benzoate | 17.7 | 5.9 | 5.2 |
| Cyclohexylbenzene | 18.6 | 1.0 | 1.6 |
| Decahydronaphthalene | 17.5 | 0.4 | 1.0 |
| Diphenyl ether | 19.9 | 2.9 | 3.3 |
| Ethyl phenyl ketone (propiophenone) | 18.3 | 8.9 | 5.3 |
| Ethylbenzene | 18.2 | 2.7 | 2.1 |
| Ethyl benzoate | 18.1 | 6.6 | 5.9 |
| Furfuryl alcohol | 18.1 | 6.7 | 11.9 |
| gamma-Terpinene | 18.0 | 2.5 | 2.8 |
| Hexylbenzene | 17.4 | 2.9 | 1.6 |
| Indane | 19.7 | 7.3 | 5.8 |
| Indene | 20.3 | 4.4 | 5.4 |
| Isoamylbenzene | 17.1 | 3.7 | 1.8 |
| Isobutylbenzene | 17.1 | 2.9 | 1.6 |
| Isopropylbenzene (cumene) | 17.8 | 2.0 | 1.1 |
| m-Cymene | 18.1 | 2.0 | 2.1 |
| Mesitylene | 19.0 | 2.9 | 1.6 |
| Methyl benzoate | 18.5 | 7.9 | 6.4 |
| Methylphenyl acetate | 18.2 | 7.3 | 6.4 |
| m-Xylene | 18.8 | 3.1 | 2.7 |
| n-Butoxybenzene | 17.5 | 4.4 | 4.1 |
| n-Butylbenzene | 17.6 | 2.6 | 1.7 |
| n-Propyl benzoate | 17.8 | 6.6 | 6.3 |
| n-Propylbenzene | 17.8 | 3.4 | 2.8 |
| o-Dichlorobenzene | 19.5 | 8.7 | 3.3 |
| o-Diethylbenzene | 17.7 | 0.7 | 1.9 |
| o-Ethyltoluene | 18.0 | 1.9 | 2.8 |
| o-Xylene | 18.4 | 2.0 | 2.9 |
| Pentylbenzene | 17.4 | 3.0 | 1.8 |
| p-Ethyltoluene | 18.3 | 3.5 | 2.8 |
| Phenetole | 18.1 | 4.6 | 4.6 |
| Phenyl acetate | 18.5 | 7.9 | 6.4 |
| p-Isopropyltoluene (p-cymene) | 18.0 | 2.5 | 2.8 |
| Propiophenone | 18.3 | 8.9 | 5.3 |
| Propyl benzoate | 17.8 | 6.6 | 6.3 |
| p-Xylene | 18.7 | 3.3 | 3.3 |
| sec-Butylbenzene | 17.2 | 2.2 | 1.6 |
| t-Butylbenzene | 17.2 | 1.3 | 2.9 |
| Tetralin | 19.1 | 2.3 | 4.0 |
| Thiophene | 18.8 | 5.2 | 7.4 |
| Toluene | 18.6 | 4.0 | 2.2 |
| Veratrol | 18.2 | 6.3 | 7.5 |

$H_d$ refers to the dispersion contribution
$H_p$ refers to the polar contribution
$H_h$ refers to the hydrogen bonding contribution The solvent preferably has a boiling point or sublimation temperature of <300° C., particularly preferably ≤260° C., especially preferably ≤220° C., at the pressure employed, very preferably at atmospheric pressure (1013 hPa). The evaporation can also be accelerated, for example through the use of heat and/or reduced pressure. Unexpected improvements can be achieved through the use of solvents having a boiling point of at least 100° C., preferably at least 130° C.

The organic solvent can usually have a surface tension of at least 28 mN/m, preferably at least 30 mN/m, particularly preferably at least 32 mN/m and especially preferably at least 35 mN/m. The surface tension can be measured using a FTA (First Ten Angstrom) 125 contact angle goniometer at 25° C. Details of the method are available from First Ten Angstrom, as published by Roger P. Woodward, Ph.D. “Surface Tension Measurements Using the Drop Shape Method”. The pendant drop method can preferably be used to determine the surface tension.

For a rough estimate, the surface tension can be calculated using the Hansen solubility parameters by means of the formula expounded in Hansen Solubility Parameters: A User’s Handbook, Second Edition, C. M. Hansen (2007), Taylor and Francis Group, LLC (HSPiP manual).

$$\text{Surface tension}=0.0146\times(2.28\times{}^{\delta}H_d^{\,2}+{}^{\delta}H_p^{\,2}+{}^{\delta}H_h^{\,2})\times MVol^{0.2},\text{ where:}$$

$H_d$ refers to the dispersion contribution
$H_p$ refers to the polar contribution
$H_h$ refers to the hydrogen bonding contribution
MVol refers to the molar volume.

The Hansen solubility parameters can be determined using the Hansen Solubility Parameters in Practice (HSPiP) program ($2^{nd}$ Edition) as available from Hanson and Abbot et al.

The solvent can preferably have a relative evaporation rate (butyl acetate=100) of at least 0.01, preferably at least 0.1, preferably at least 0.5, particularly preferably at least 5, very particularly preferably at least 10 and especially preferably at least 20. The relative evaporation rate can be determined in accordance with DIN 53170: 2009-08. For a rough estimate, the relative evaporation rate can be calculated using the Hansen solubility parameters using the HSPiP program as mentioned above and below.

The formulation of the present invention preferably comprises at least 70% by weight, particularly preferably at least 80% by weight and especially preferably at least 90% by weight of one or more organic solvents.

In a further preferred embodiment, the formulation of the present invention comprises at least one polymeric material as inert binder. This means that the polymer does not have semiconductor properties or react chemically with one of the semiconductor compounds in the composition. The low conducting properties of the inert polymeric binder can be determined as low permittivity. Preferred binders in accordance with the present invention are materials having a low dielectric constant, i.e. those having a dielectric constant (E)

at 1,000 Hz of 3.3 or less. The organic binder preferably has a dielectric constant at 1,000 Hz of less than 3.0, more preferably 2.9 or less. The organic binder preferably has a dielectric constant at 1,000 Hz of greater than 1.7. The dielectric constant of the binder is particularly preferably in the range from 2.0 to 2.9. The term "react chemically" as used above and below denotes a possible oxidation or other chemical reaction of the non-conductive additive with the organic light-emitting materials and/or charge-transport materials under the conditions used for the production, storage, transport and/or use of the formulation and the OLED device.

The polymeric binder preferably has a weight average molecular weight in the range from 1,000 to 50,000,000 g/mol, particularly preferably 1,500 to 10,000,000 g/mol and especially preferably 2,000 to 5,000,000 g/mol. Surprising effects can be achieved with polymers having a weight average molecular weight of preferably ≥10,000 g/mol, particularly preferably ≥100,000 g/mol.

In particular, the polymer can have a polydispersity index $M_w/M_n$ in the range from 1.0 to 10.0, particularly preferably in the range from 1.1 to 5.0 and especially preferably in the range from 1.2 to 3.

The polymeric binder is usually dispersible or soluble in the solvent of the present composition as described above and below. The polymeric binder is preferably soluble in the organic solvent, and the solubility of the polymeric binder in the solvent is at least 1 g/l, particularly preferably at least 5 g/l and a specially preferably at least 10 g/l.

According to a particular embodiment of the present invention, the composition can preferably comprise 0.1 to 10% by weight, particularly preferably 0.25 to 5% and especially preferably 0.5 to 4% by weight of polymeric binder.

According to a particular embodiment, the polymeric binders preferably contain recurring units derived from styrene and/or olefins. Preferred polymeric binders can contain at least 80% by weight, preferably 90% by weight and particularly preferably 99% by weight of recurring units derived from styrene monomers and/or olefins.

Styrene monomers are well known in the art. These monomers include styrene, substituted styrenes with an alkyl substituent in the side chain, such as α-methylstyrene and α-ethylstyrene, substituted styrenes with an alkyl substituent on the ring, such as vinyltoluene and p-methylstyrene, halogenated styrenes, such as monochiorostyrenes, dichlorostyrenes, tri-bromostyrenes and tetrabromostyrenes.

Olefins are monomers consisting of hydrogen and carbon atoms. These monomers include ethylene, propylene, butylene, isoprene and 1,3-buta-diene.

According to a particular aspect of the present invention, the polymeric binder is polystyrene having a weight average molecular weight in the range from 50,000 to 2,000,000 g/mol, preferably 100,000 to 750,000 g/mol, particularly preferably in the range from 150,000 to 600,000 g/mol and especially preferably in the range from 200,000 to 500,000 g/mol.

According to a further embodiment of the present invention, the polymeric binder is poly-4-methylstyrene having a weight average molecular weight in the range from 40,000 to 120,000 g/mol, particularly preferably in the range from 60,000 to 100,000 g/mol.

In particular, the binder can be poly-α-methylstyrene having a weight average molecular weight in the range from 1,000 to 20,000 g/mol, particularly preferably in the range from 1,500 to 6,000 g/mol.

Useful and preferred polymeric binders have Hansen solubility parameters $H_d$ in the range from 15.7 to 23.0 $MPa^{0.5}$, $H_p$ in the range from 0.0 to 20.0 $MPa^{0.5}$ and $H_h$ in the range from 0.0 to 12.5 $MPa^{0.5}$. Particularly preferred polymeric binders have Hansen solubility parameters $H_d$ in the range from 17.0 to 21.0 $MPa^{0.5}$, $H_p$ in the range from 1.0 to 5.0 $MPa^{0.5}$ and $H_h$ in the range from 2.0 to 10.0 $MPa^{0.5}$. Especially preferred polymeric binders have Hansen solubility parameters $H_d$ in the range from 19.0 to 21.0 $MPa^{0.5}$, $H_p$ in the range from 1.0 to 3.0 $MPa^{0.5}$ and $H_h$ in the range from 2.5 to 5.0 $MPa^{0.5}$.

The Hansen solubility parameters can be determined using the Hansen Solubility Parameters in Practice (HSPiP) program (2$^{nd}$ edition) as available from Hanson and Abbot et al.

Examples of useful polymeric binders are disclosed in Table 1 of WO 2011/076325 A1.

According to a preferred embodiment of the present invention, the inert binder is a polymer having a glass transition temperature in the range from −70 to 160° C., preferably 0 to 150° C., particularly preferably 50 to 140° C. and especially preferably 70 to 130° C. The glass transition temperature can be determined by measuring the DSC of the polymer (DIN EN ISO 11357, heating rate 10° C. per minute).

The formulation according to the present invention may additionally comprise one or more further components, such as, for example, surface-active compounds, lubricants, wetting agents, dispersants, hydro-phobicising agents, adhesives, flow improvers, antifoams, deaerators, diluents, which may be reactive or non-reactive, assistants, colorants, dyes or pigments, sensitisers, stabilisers, nanoparticles or inhibitors. However, these further components should not be oxidising or otherwise capable of reacting chemically with the organic semiconductor material or exert an electrically doping effect on the organic semiconductor material.

Surprising improvements can be achieved by means of volatile wetting agents. The term "volatile" as used above and below means that the agent can be removed from the organic semiconductor material(s) by evaporation, after these material(s) have been deposited on a substrate of an OLED device, under conditions (such as temperature and/or reduced pressure) which do not significantly damage these materials or the OLED device. This preferably means that the wetting agent has a boiling point or sublimation temperature of <350° C., particularly preferably ≤300° C., especially preferably ≤250° C., at the pressure employed, very preferably at atmospheric pressure (1013 hPa). The evaporation can also be accelerated, for example through the use of heat and/or reduced pressure.

Surprising effects can be achieved using formulations comprising volatile components having similar boiling points. The difference between the boiling point of the wetting agent and the organic solvent is preferably in the range from −50° C. to 50° C., particularly preferably in the range from −30° C. to 30° C. and especially preferably in the range from −20° C. to 20° C.

Preferred wetting agents are non-aromatic compounds. The wetting agents are further preferably non-ionic compounds. Particular useful wetting agents have a surface tension of at most 35 mN/m, preferably at most 30 mN/m, and particularly preferably at most 25 mN/m. The surface tension can be measured using a FTA (First Ten Angstrom) 125 contact angle goniometer at 25° C. Details of the method are available from First Ten Angstrom as published by Roger P. Woodward, Ph.D. "Surface Tension Measurements Using the Drop Shape Method". The pendant drop method can preferably be used to determine the surface tension.

According to a particular aspect of the present invention, the difference between the surface tension of the organic solvent and the wetting agent is preferably at least 1 mN/m, preferably at least 5 mN/m and particularly preferably at least 10 mN/m.

According to a particular aspect of the present invention, the wetting additive can have a relative evaporation rate (butyl acetate=100) of at least 0.01, preferably at least 0.1, preferably at least 0.5, particularly preferably at least 5, very particularly preferably at least 10 and especially preferably at least 20.

Unexpected improvements can be achieved using compositions comprising solvents and wetting agents having a similar relative evaporation rate (butyl acetate=100). The difference between the relative evaporation rate (butyl acetate=100) of the wetting agent and the organic solvent is preferably in the range from −20 to 20, particularly preferably in the range from −10 to 10. According to a preferred embodiment of the present invention, the ratio of the relative evaporation rate (butyl acetate=100) of the wetting agent to the relative evaporation rate (butyl acetate=100) of the organic solvent can range from 230:1 to 1:230, preferably from 20:1 to 1:20 and particularly preferably from 5:1 to 1:5.

Unexpected improvements can be achieved by wetting agents having a molecular weight of at least 100 g/mol, preferably at least 150 g/mol, particularly preferably at least 180 g/mol and especially preferably at least 200 g/mol.

Suitable and preferred wetting agents which do not oxidise or otherwise react chemically with the USC materials are selected from the group consisting of siloxanes, alkanes, amines, alkenes, alkynes, alcohols and/or halogenated derivates of these compounds. Furthermore, fluoro ethers, fluoro esters and/or fluoro ketones can be used. These compounds are particularly preferably selected from methylsiloxanes having 6 to 20 carbon atoms, in particular 8 to 16 carbon atoms; $C_7$-$C_{14}$ alkanes, $C_7$-$C_{14}$ alkenes, $C_7$-$C_{14}$ alkynes, alcohols having 7 to 14 carbon atoms, fluoro ethers having 7 to 14 carbon atoms, fluoro esters having 7 to 14 carbon atoms and fluoro ketones having 7 to 14 carbon atoms. Especially preferred wetting agents are methylsiloxanes having 8 to 14 carbon atoms.

Examples of compounds which are useful and preferred as wetting agents are disclosed in WO 2011/076325 A1.

The formulation preferably comprises at most 5% by weight, particularly preferably at most 3% by weight and especially preferably at most 1% by weight of wetting additives. The composition preferably comprises 0.01 to 5% by weight, particularly preferably 0.05 to 3% by weight and especially preferably 0.1 to 1% by weight of wetting agent.

The formulation according to the invention may comprise further compounds. The further compounds can be inorganic or organic compounds. The further compounds are preferably organic semiconductor materials, which are very preferably selected from the group consisting of fluorescent emitters, phosphorescent emitters, host materials, matrix materials, electron-transport materials, electron-injection materials, hole-conductor materials, hole-injection materials, n-dopants, wide-band-gap materials, electron-blocking materials and hole-blocking materials.

Fluorescent emitters (also called fluorescent dopants) in the sense of the present invention are compounds in which the light emission takes place through a spin-allowed transition, preferably a transition from an excited singlet state.

The term phosphorescent emitters (also called phosphorescent dopants) typically encompasses compounds in which the light emission takes place through a spin-forbidden transition, for example a transition from a triplet state or a state having a higher spin quantum number, for example a quintet state, the transition is preferably a transition from a triplet state.

Suitable phosphorescent dopants are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent dopants used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present application, all luminescent iridium, platinum or copper complexes are regarded as phosphorescent compounds.

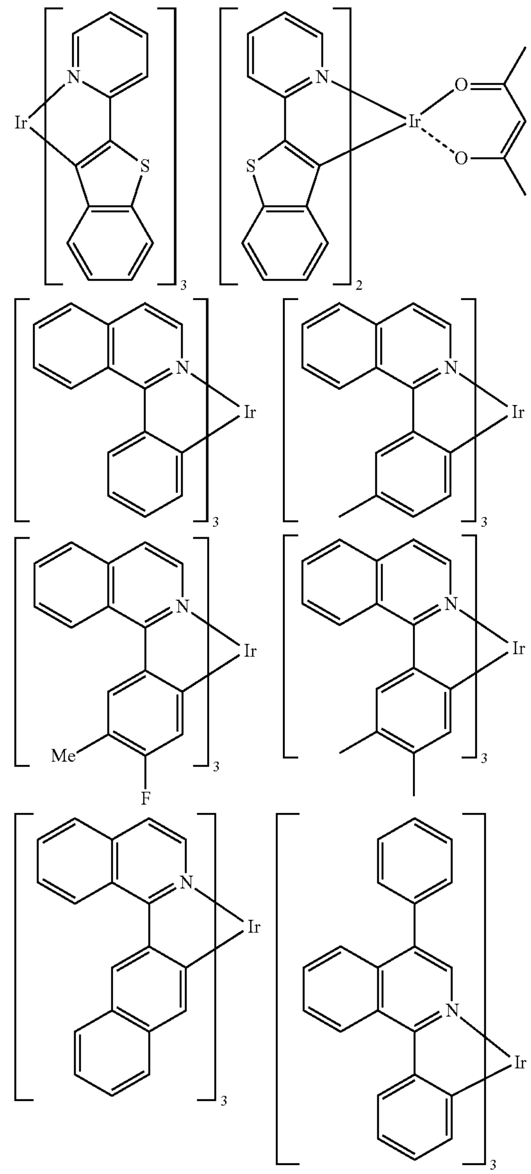

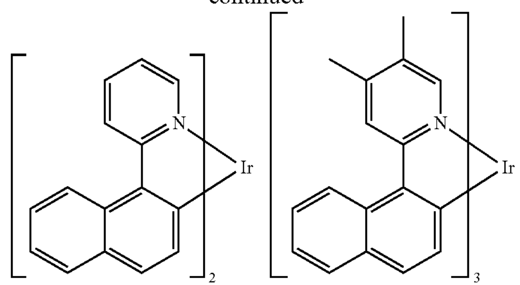
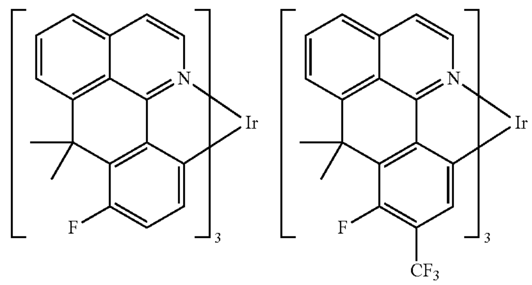
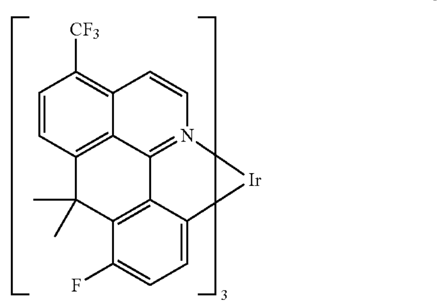
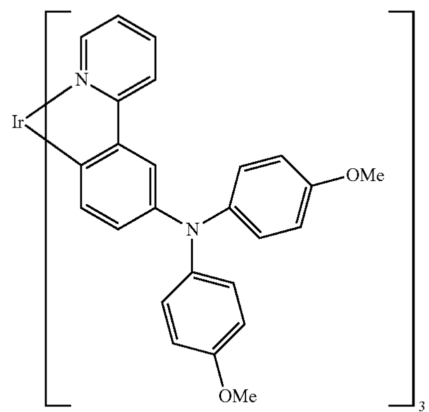
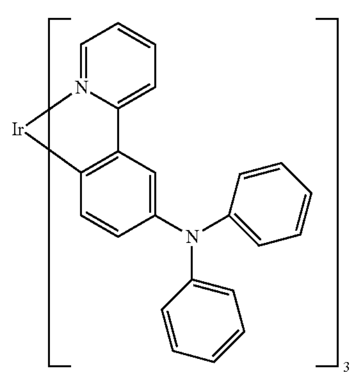
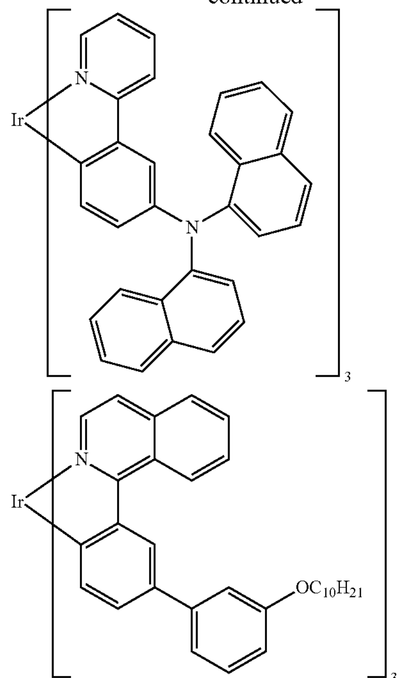
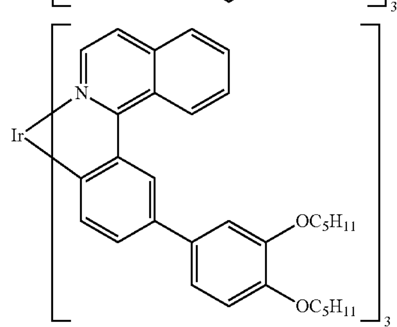
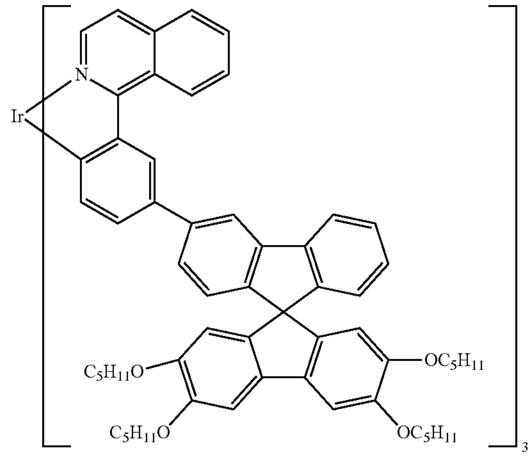
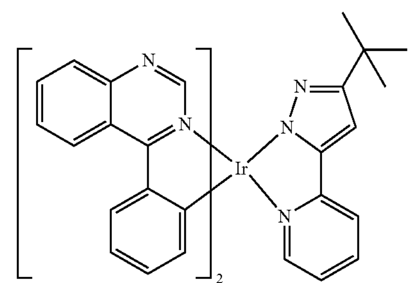

-continued
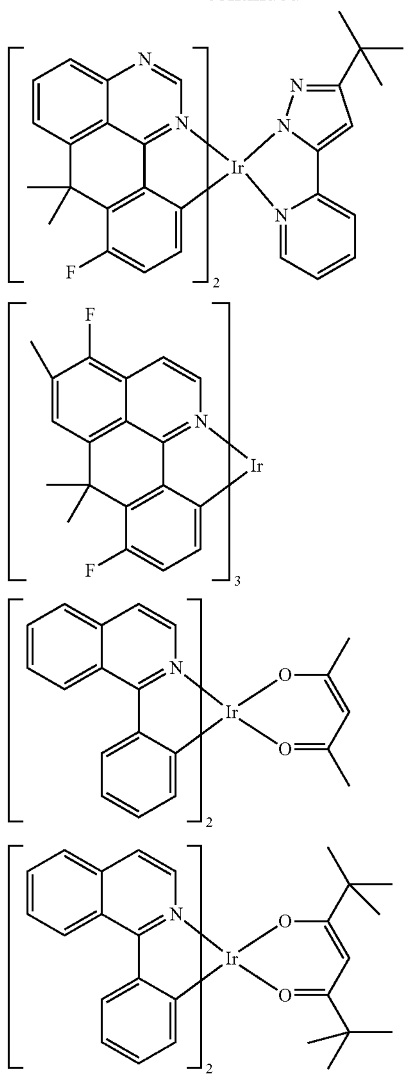
-continued
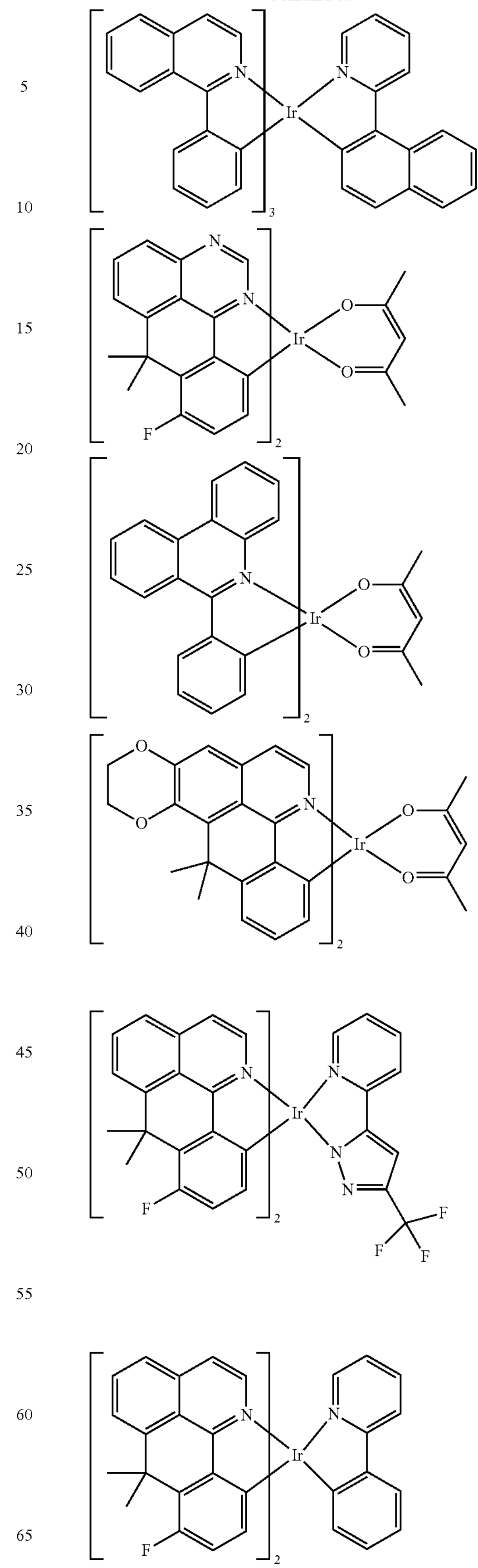

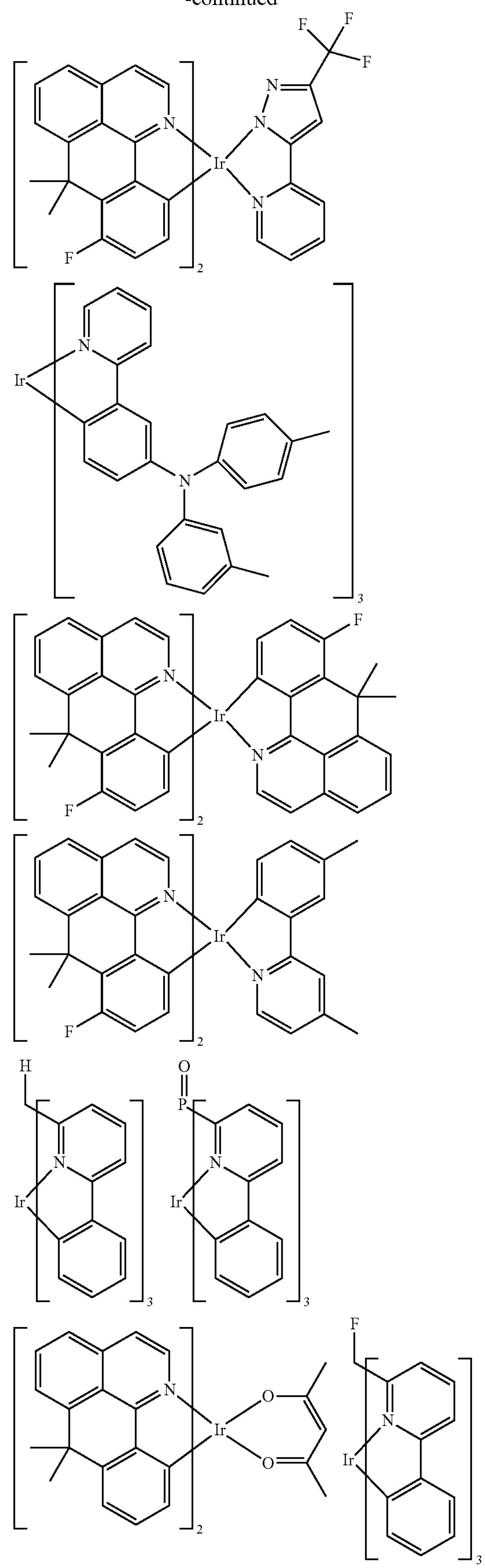
F
F
F
N
N
N
Ir
N
F
2
N
Ir
N
3
F
N
Ir
N
F
2
N
Ir
N
F
2
H
O
P
N
Ir
3
N
Ir
3
N
O
Ir
O
2
F
N
Ir
3
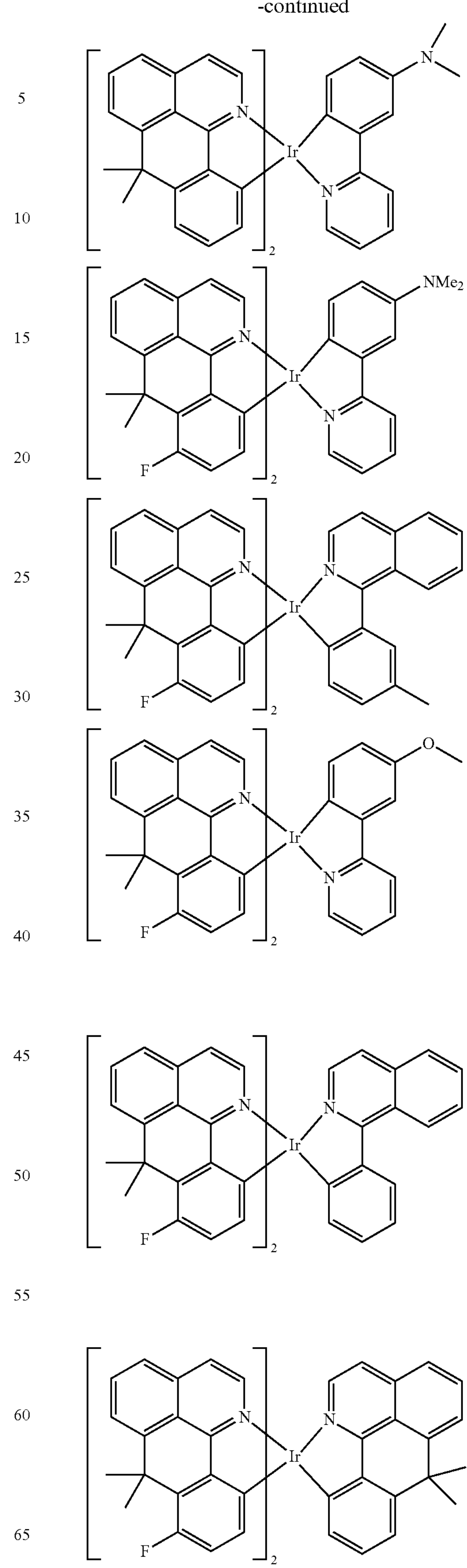
N
N
Ir
N
2
NMe2
N
Ir
N
F
2
N
N
Ir
F
2
O
N
Ir
N
F
2
N
N
Ir
F
2
N
N
Ir
F
2

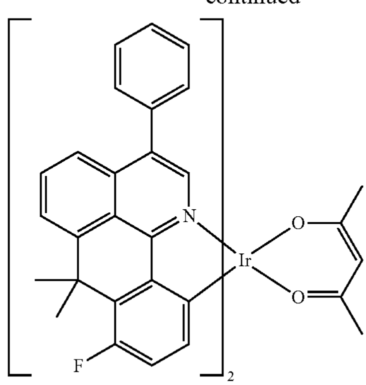
N
Ir
O
O
F
2
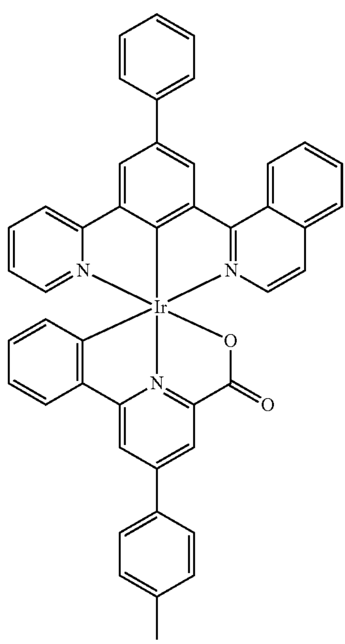
N
N
Ir
O
N
O
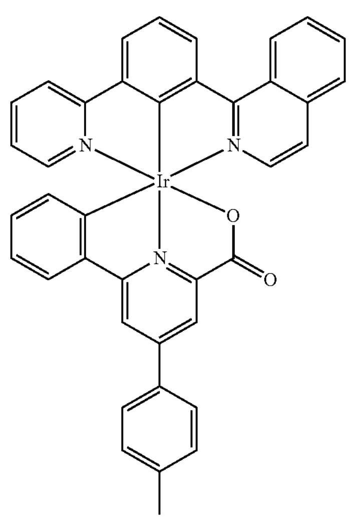
N
N
Ir
O
N
O
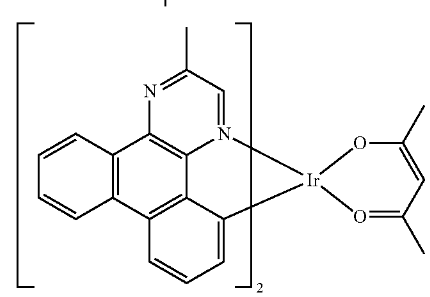
N
N
Ir
O
O
2
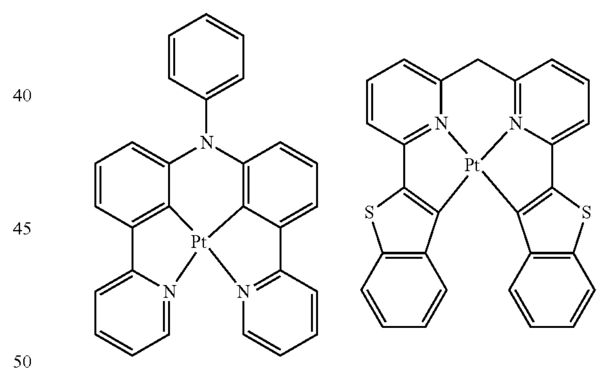
N
Pt
N
N
N
N
Pt
S
S
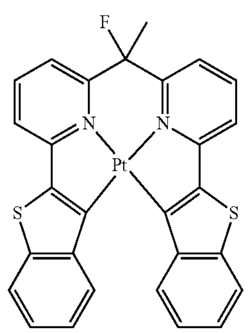
F
N
N
Pt
S
S
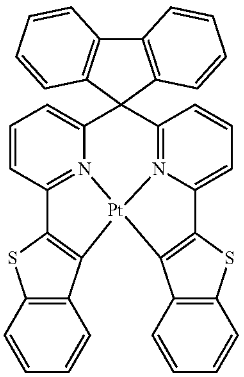
N
N
Pt
S
S
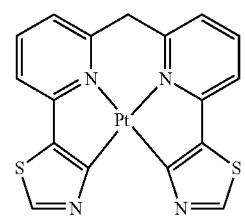
N
N
Pt
S
N
N
S -continued
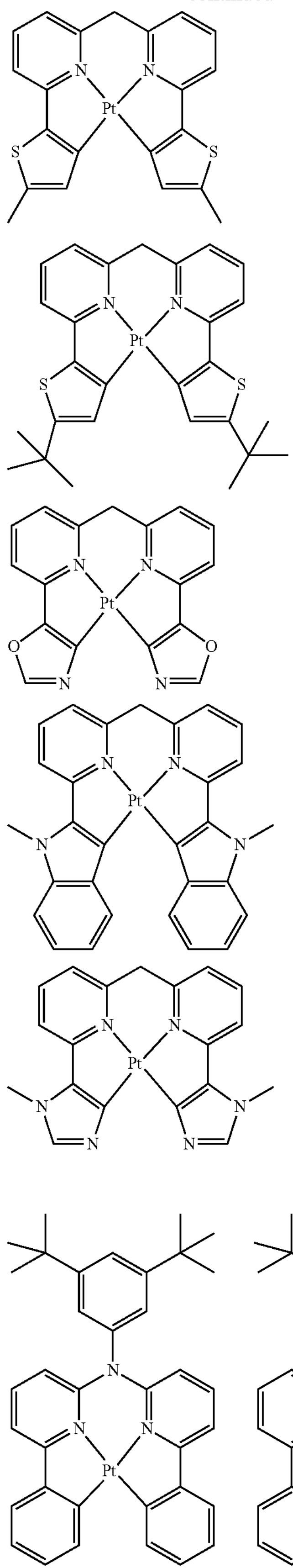
-continued
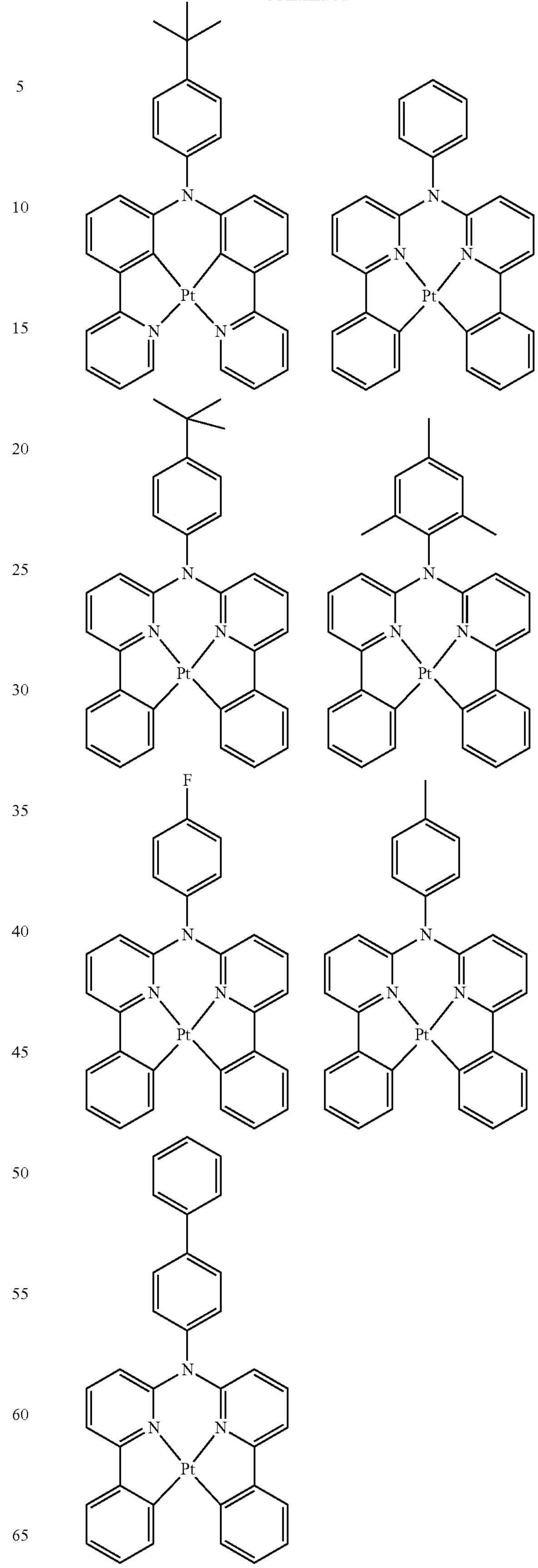

-continued
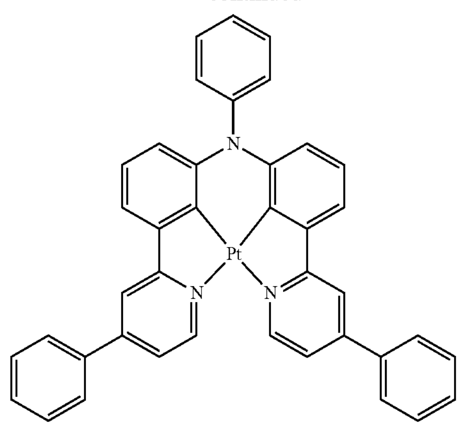
-continued
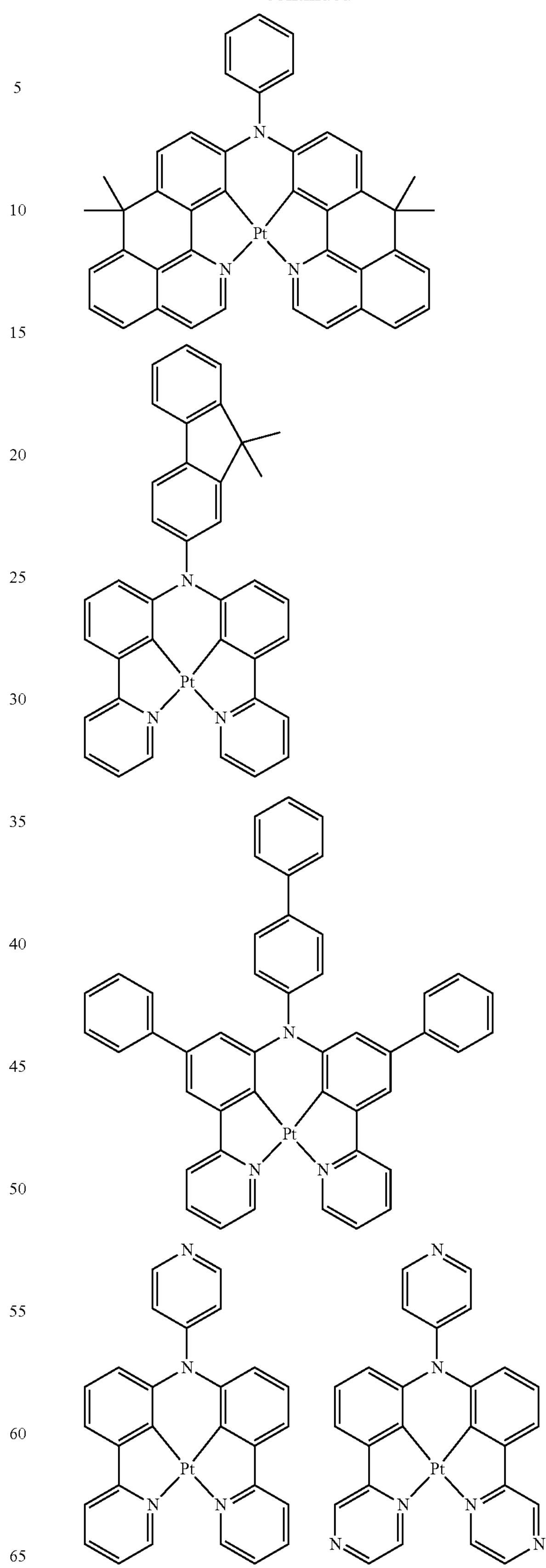

-continued
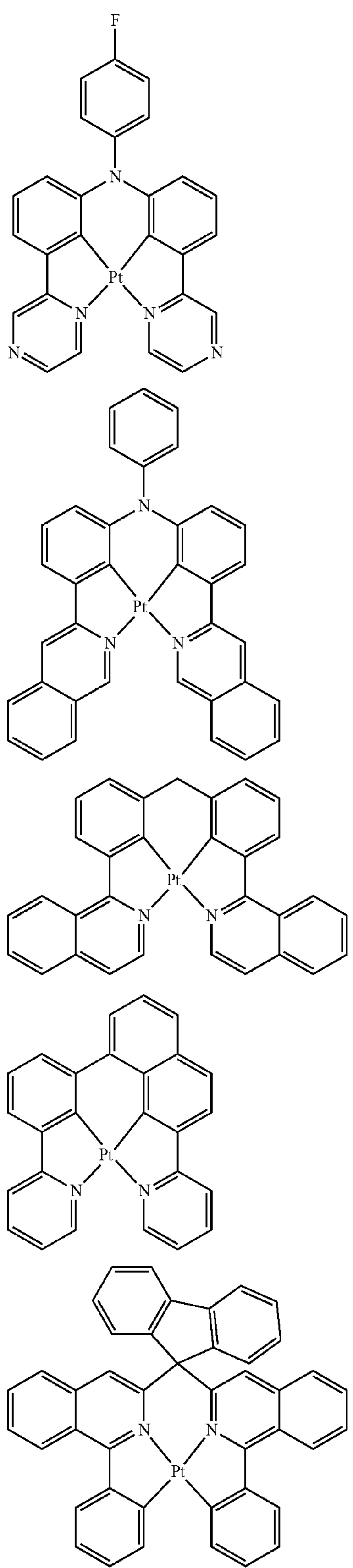
-continued
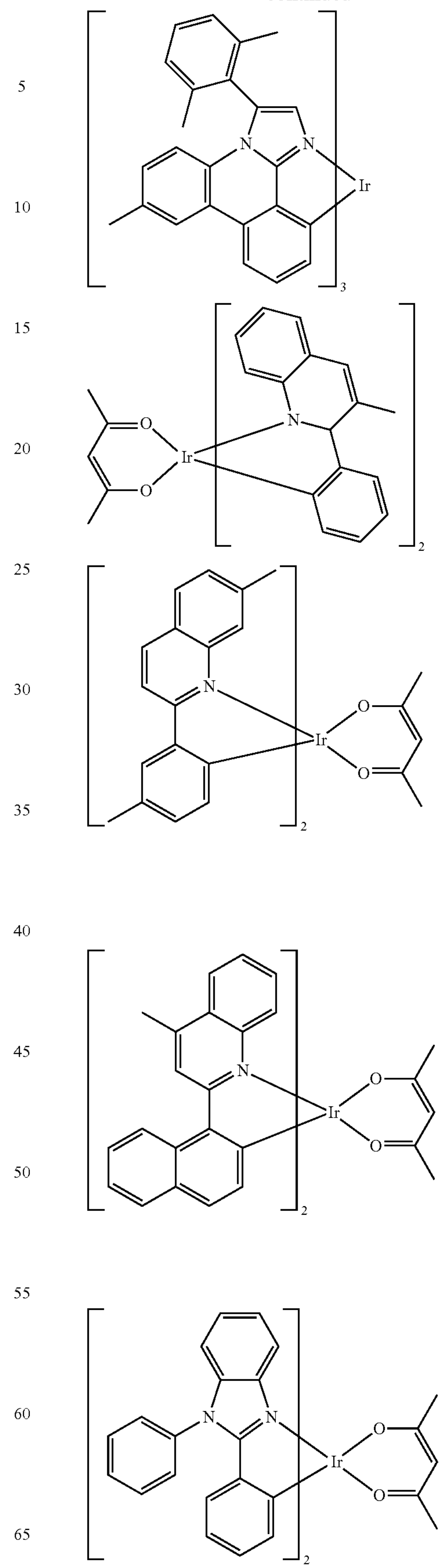

-continued
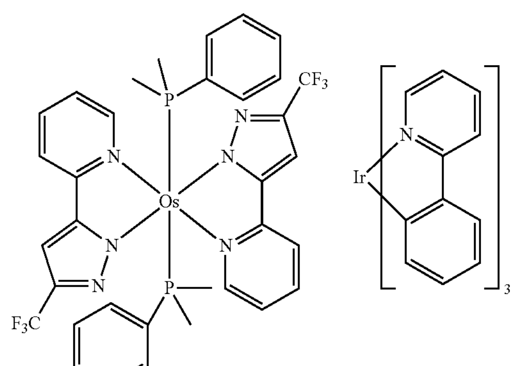
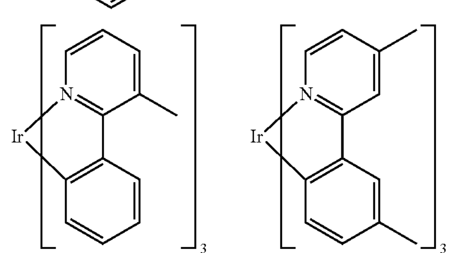
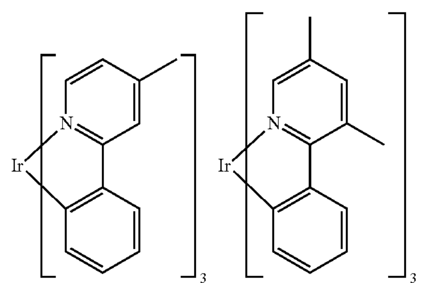
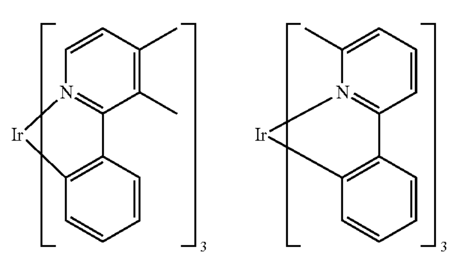
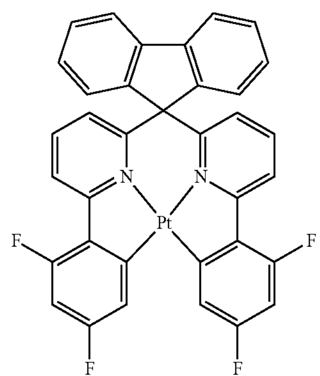
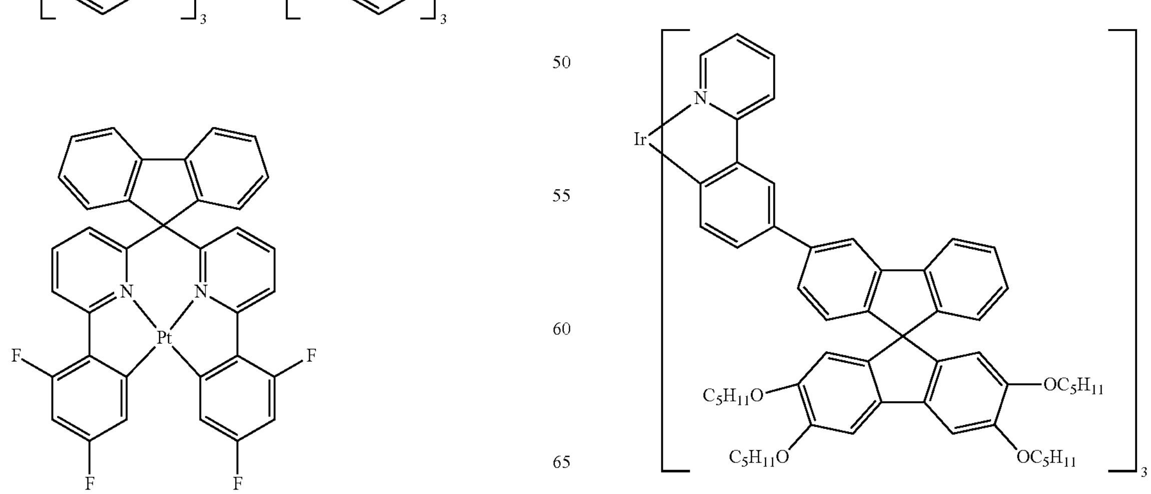
-continued
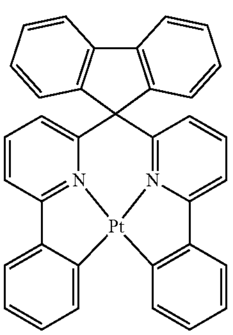
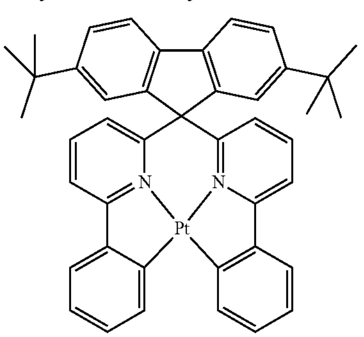
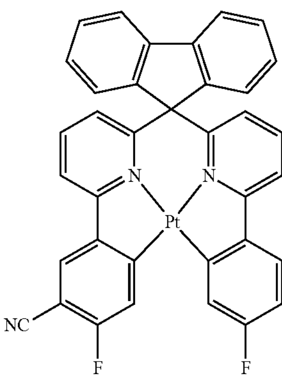
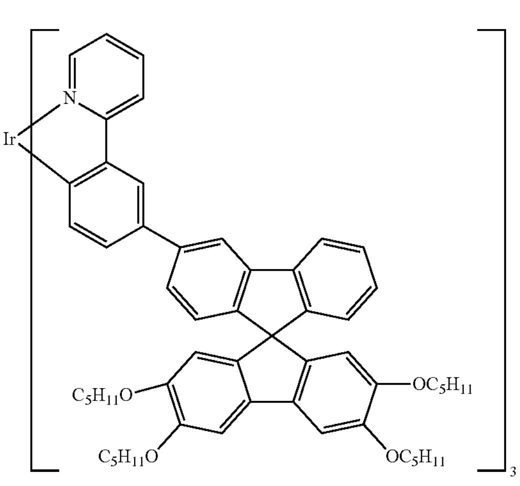

-continued
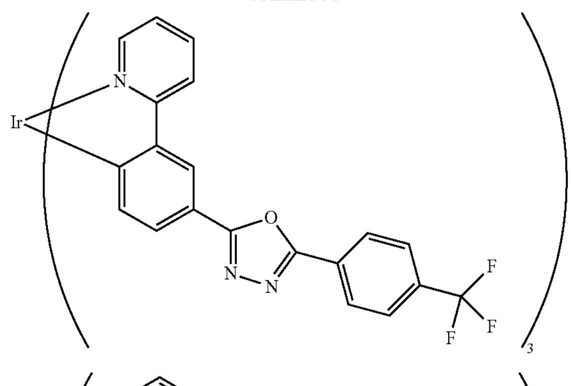
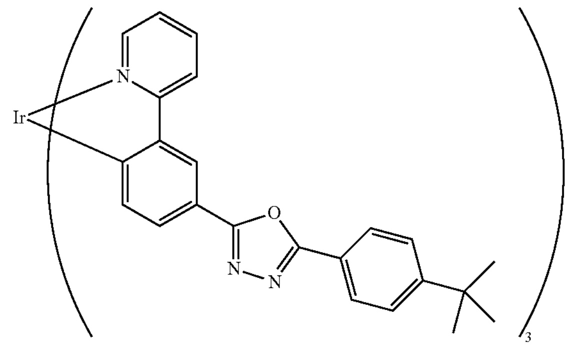
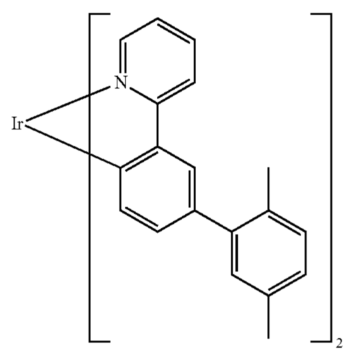
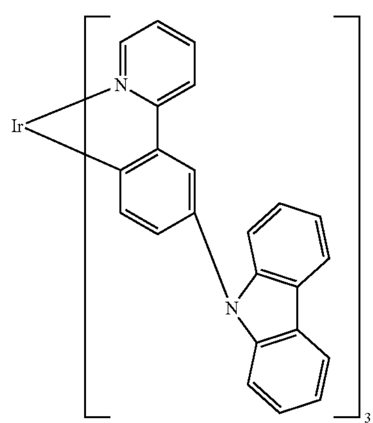
-continued
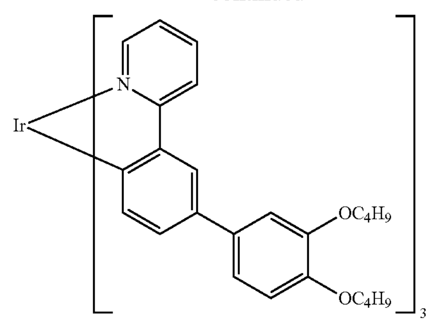
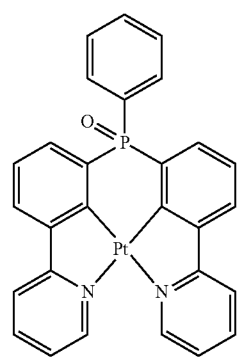
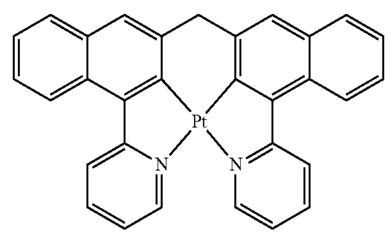
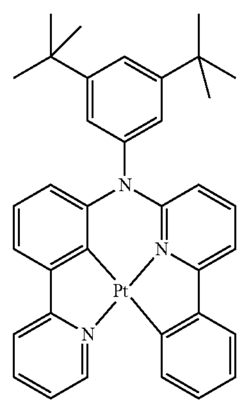
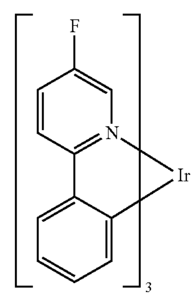
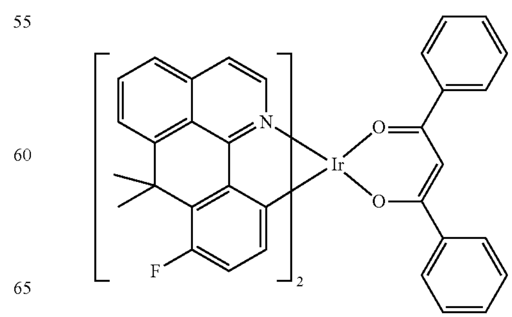

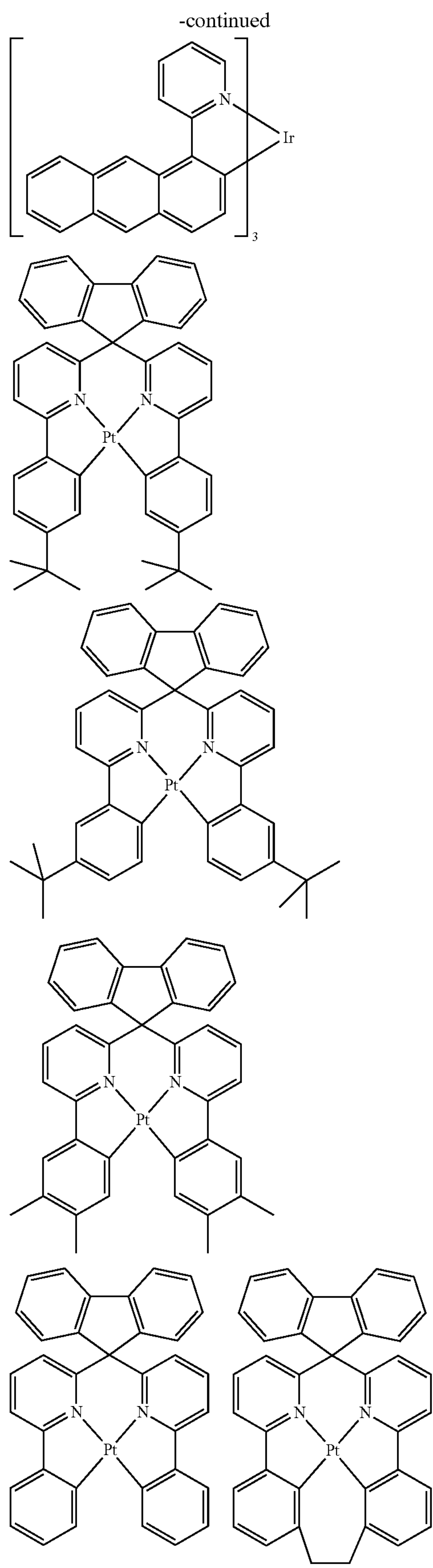
Ir
N
Pt
3
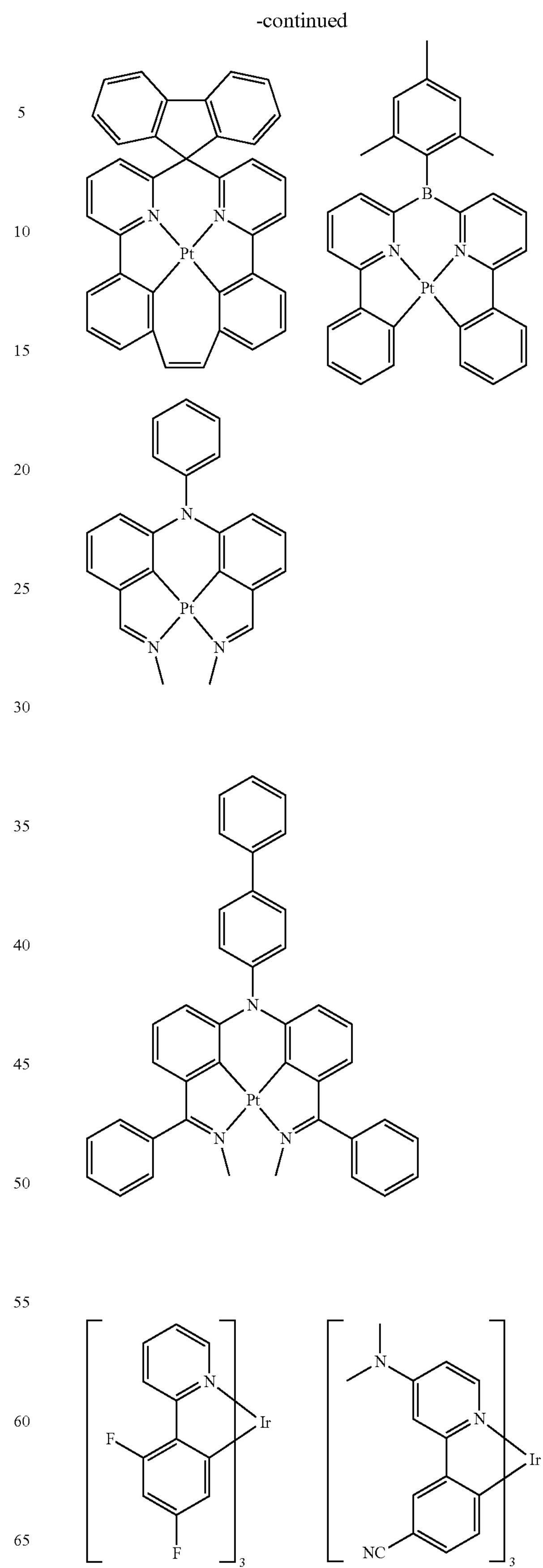
N
Pt
B
F
NC
Ir
3

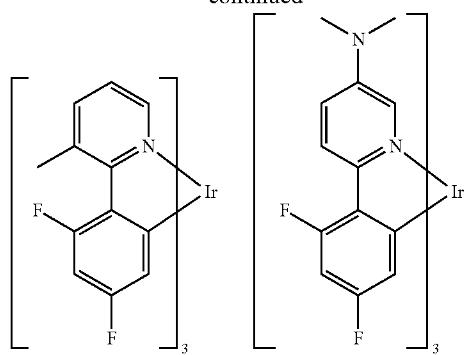
N
Ir
F
F
3
N
N
Ir
F
F
3
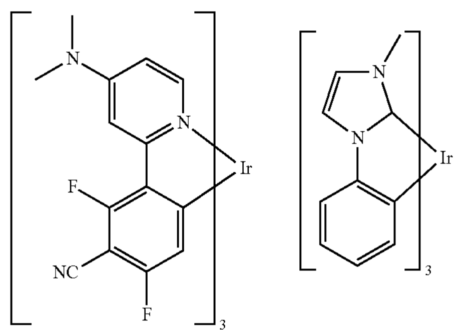
N
N
Ir
F
NC
F
3
N
N
Ir
3
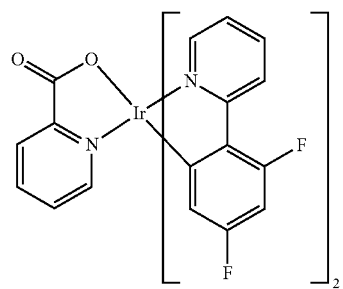
O
O
Ir
N
N
F
F
2
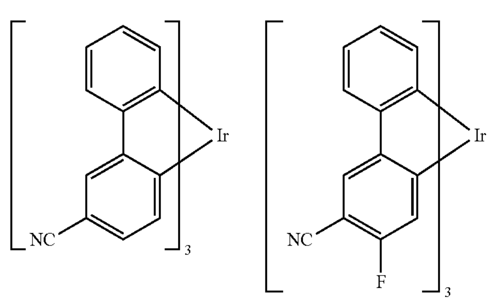
Ir
NC
3
Ir
NC
F
3
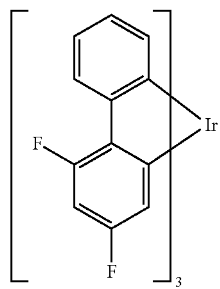
Ir
F
F
3
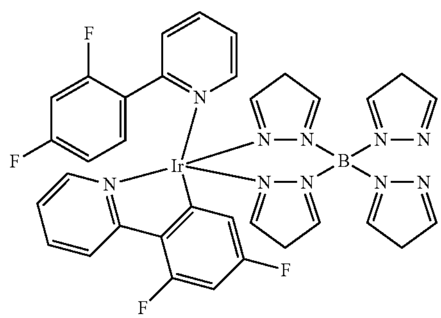
F
N
F
Ir
N
N
N
B
N
N
N
N
N
N
F
F
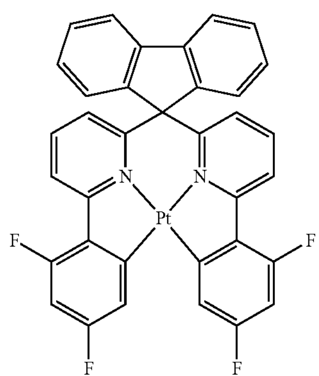
N
N
Pt
F
F
F
F
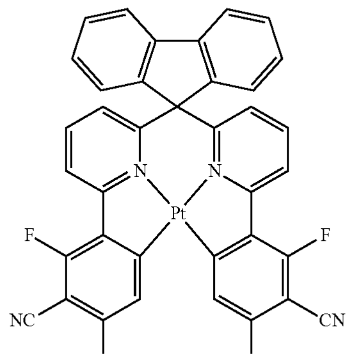
N
N
Pt
F
F
NC
CN
F
F
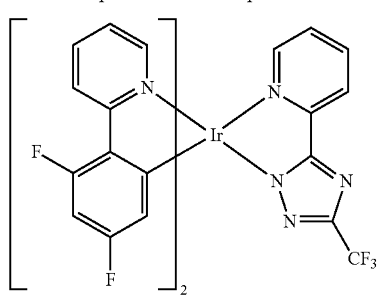
N
N
Ir
F
N
N
N
F
CF3
2
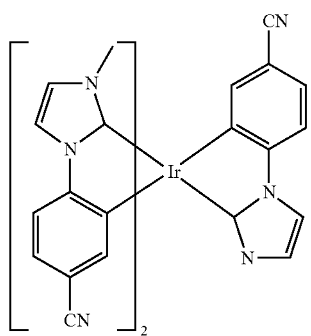
CN
N
N
Ir
N
N
CN
2

-continued
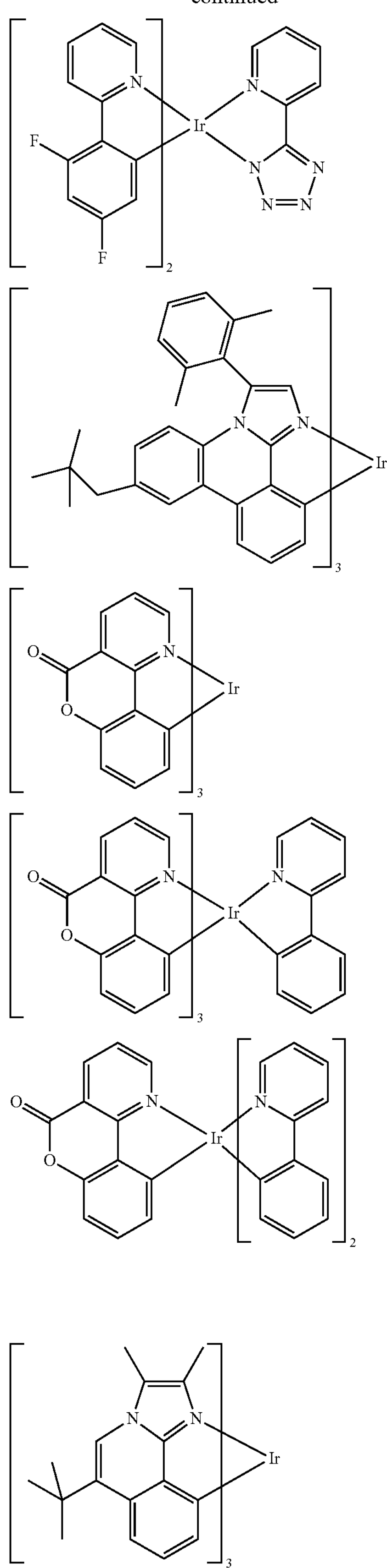
-continued
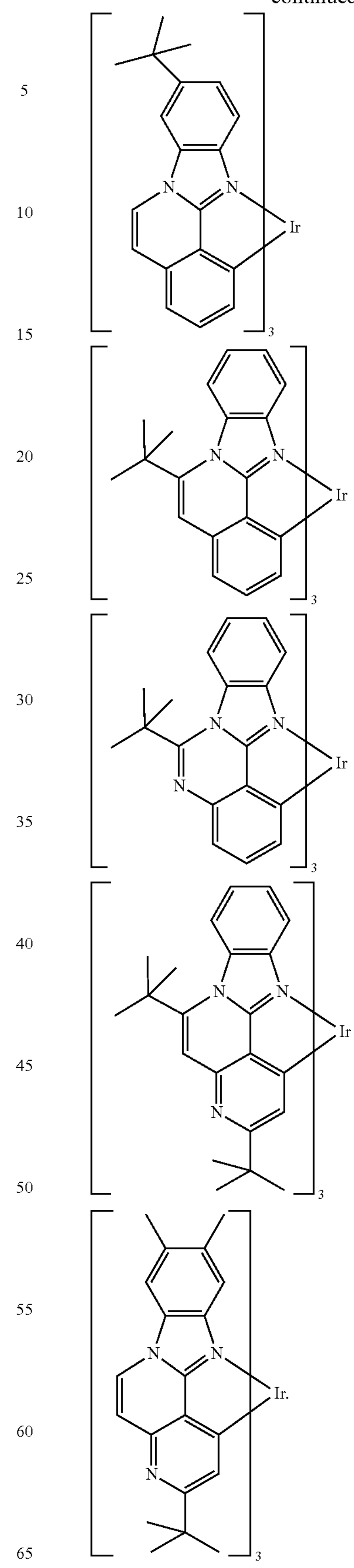

A dopant in a system comprising a matrix material and a dopant is in the present application generally taken to mean the component whose proportion in the mixture is the smaller. Correspondingly, a matrix material in a system comprising a matrix material and a dopant is taken to mean the component whose proportion in the mixture is the greater.

The above-mentioned further compounds which may be present in the formulations according to the invention are well known to the person skilled in the art. The person skilled in the art will therefore be able to make a selection from a large range of known compounds.

In a preferred embodiment, the formulation comprises, as further compound, at least one organic matrix material, where the organic matrix materials are preferably carbazoles, indenocarbazoles, indolocarbazoles (for example EP 13001800.5), triazines, pyrimidines, lactams, ketones, phosphine oxides, as disclosed, for example, in EP 13001797.3, triphenylenes, diarylfluorenes (in particular 9,9-diarylfluorenes, as disclosed in WO 2009/124627) or dibenzofurans.

The matrix material is preferably a hole-conducting matrix material, which is preferably selected from the group of the carbazoles, indenocarbazoles and indolocarbazoles.

Furthermore, the matrix material is preferably an electron-conducting matrix material, which is preferably selected from the group of the triazines, pyrimidines, lactams, ketones and phosphine oxides.

Furthermore the formulation preferably comprises a triphenylene matrix. Typical triphenylene matrix compounds which are preferred for the purposes of the present invention are disclosed in EP 1888708.

The formulation also preferably comprises a dibenzofuran matrix.

The organic matrix material present in the formulation and the TADF compound preferably satisfy the following condition:

$$[\text{LUMO(TADF)}-\text{HOMO(matrix)}] \text{ is greater than or equal to } [S_1(\text{TADF})-0.4 \text{ eV}],$$

where $S_1$(TADF) is the first excited singlet state $S_1$ of the TADF compound. LUMO(TADF) is the LUMO energy of the TADF compound and HOMO-(matrix) is the HOMO energy of the matrix.

The formulation, besides a first matrix material very particularly preferably also comprises a second matrix material. Mixed-matrix systems exhibit particularly advantageous effects. Electronic devices comprising these mixed-matrix systems frequently have very good performance data. Mixed-matrix systems are disclosed, for example, in U.S. Pat. No. 6,392,250 B1 and in U.S. Pat. No. 6,803,720 B2.

It is very particularly preferred for the first matrix material to be an electron-transporting matrix material and for the second matrix material to be a hole-transporting matrix material; the electron-transporting matrix materials are preferably triazines, pyrimidines, lactams, ketones or phosphine oxides; the hole-transporting matrix materials are preferably carbazoles, indenocarbazoles or indolocarbazoles.

It is furthermore very particularly preferred for both the first matrix material and also the second matrix material to be electron-transporting matrix materials, which are preferably triazines, pyrimidines, lactams, ketones or phosphine oxides.

It is also preferred for both the first matrix material and also the second matrix material to be hole-transporting matrix materials, which are preferably carbazoles, indenocarbazoles or indolocarbazoles.

It is especially preferred for the first matrix material to be either an electron-transporting matrix material or a hole-transporting matrix material and for the second matrix material to be a compound which has a large band gap. These compounds are also called wide-band-gap materials (U.S. Pat. No. 7,294,849).

The wide-band-gap material preferably has a band gap of 2.5 eV or more, preferably 3.0 eV or more, very preferably 3.2 eV or more, very particularly preferably 3.5 eV or more and especially preferably 3.7 eV or more. The band gap in the present application is calculated from the difference of the energy levels of the HOMO and LUMO.

The TADF compound can be employed as emitter in electronic devices. In a further embodiment of the present invention, the TADF compound can also be used as matrix material. In this case, the TADF compound transfers its energy to an emitter, which ultimately emits radiation from the electronic device. Any emitter is basically suitable for this purpose. The use of TADF compounds as matrix makes electronic devices having particularly advantageous performance data possible. It is particularly preferred for the emitter to be a nanoparticle.

It is therefore very advantageous for the formulation to comprise nanocrystalline compounds or nanoparticles. The nanocrystals and nanoparticles include quantum dots and quantum rods. With the aid of these compounds, efficient OLEDs and other organic electronic devices which have a very low failure rate and exhibit emissions having narrow bands can be produced inexpensively. Furthermore, emitting devices can be obtained which exhibit excellent colour purities and colour qualities (CRI—colour rendering index). Furthermore, the emission colour (CIE 1931 RGB) of such OLEDs can be adjusted very easily and accurately.

It is very particularly preferred for the formulation, besides nanoparticles and TADF compound(s), also to comprise further matrix compounds, which are preferably the above-mentioned electron-transporting matrix compounds or the above-mentioned hole-transporting matrix compounds.

Both quantum dots and also quantum rods can be produced very simply. The size of the particles, which represents the determining factor for the colour of the emitted radiation, can easily be adjusted. Furthermore, the quantum dots and quantum rods are soluble in many common solvents and are very suitable for solution-based production processes.

The first monodisperse colloidal quantum dots comprising a semiconducting material were based on CdE (E=S, Se, Te) and were produced with the aid of the so-called TOPO (trioctylphosphine oxide) method (J. Am. Chem. Soc. 115 [19], 8706-8715, 1993).

A multiplicity of methods for the production of quantum dots and quantum rods is known to the person skilled in the art, preference being given to the use of solution-based methods of colloidal systems for the controlled growth of inorganic quantum dots (Science 271:933 (1996); J. Am. Chem. Soc. 30:7019-7029 (1997); J. Am. Chem. Soc. 115: 8706 (1993)).

Suitable semiconductors which are used in quantum dots and quantum rods are selected from the group consisting of elements from groups II to VI, such as, for example, CdSe, CdS, CdTe, ZnSe, ZnO, ZnS, ZnTe, HgS, HgSe, HgTe and mixtures thereof, such as, for example, CdZnSe;

elements from groups III to V, such as, for example, InAs, InP, GaAs, GaP, InN, GaN, InSb, GaSb, AlP, AlAs, AlSb and mixtures thereof, such as, for example, InAsP, CdSeTe, ZnCdSe, InGaAs;

elements from groups IV to VI, such as, for example, PbSe, PbTe and PbS and mixtures thereof;

elements from groups III to VI, such as, for example, InSe, InTe, InS, GaSe and mixtures thereof, such as, for example, InGaSe, InSeS;

elements from group IV semiconductors, such as, for example, Si and Ge and mixtures thereof, and mixtures of the above-mentioned materials.

Furthermore suitable semiconductors for quantum dots and quantum rods include those which are disclosed in U.S. Ser. No. 10/796,832 and include any type of semiconductors containing elements from groups II to VI, III to V, IV to VI and IV semiconductors. A selection of particularly suitable semiconductors is Si, Ge, Sn, Se, Te, B, C (also diamond), P, BN, BP, BAs, AlN, AlP, AlAs, AlS, AlSb, BaS, BaSe, BaTe, CaS, CaSe, CaTe, GaN, GaP, GaAs, GaSb, InN, InP, InAs, InSb, AlN, AlP, AlAs, AlSb, GaN, GaP, GaAs, GaSb, ZnO, ZnS, ZnSe, ZnTe, CdS, CdSe, CdTe, HgS, HgSe, HgTe, BeS, BeSe, BeTe, MgS, MgSe, GeS, GeSe, GeTe, SnS, SnSe, SnTe, PbO, PbS, PbSe, PbTe, CuF, CuCl, CuBr, CuI, $Si_3N_4$, $Ge_3N_4$, $Al_2O_3$, $(Al, Ga, In)_2$ $(S, Se, Te)_3$, $Al_2CO$, and a suitable combination of two or more of the said semiconductors.

It is preferred for the quantum dots or quantum rods to be selected from elements from groups II-VI, III-V, IV-VI and IV semiconductors, very preferably from ZnO, ZnS, ZnSe, ZnTe, CdS, CdSe, CdTe, HgS, HgSe, HgTe, MgS, MgSe, GeS, GeSe, GeTe, SnS, SnSe, SnTe, PbO, PbS, PbSe, PbTe, GaN, GaP, GaAs, GaSb, InN, InP, InAs, InSb, AlN, AlP, AlAs, AlSb, GaN, GaP, GaAs, GaSb, and a combination thereof.

In QDs and QRs, photoluminescence and electroluminescence arise from the band edge states of the nanoparticle. The radiative band-edge emission from nanoparticles competes with non-radiative decay channel originating from surface electronic states, as reported by X. Peng, et al., J. Am, Chem. Soc. Vol 119:7019-7029 (1997).

Quantum dots and quantum rods which have a core/shell structure have also proven particularly advantageous (J. Am. Chem. Soc. Vol 119:7019-7029 (1997)).

Core/shell structures can be obtained if organometallic precursors which contain the shell materials are used as precursors. These precursors are added to a reaction mixture with the core nanoparticle. Further details on the production process are well known to the person skilled in the art from the prior art.

In a preferred embodiment, ZnS is used as shell material.

It is furthermore preferred for the quantum dots and quantum rods to be semiconducting materials from groups II-VI, mixtures thereof and core/shell structures thereof. CdSe, CdS, CdTe, ZnSe, ZnS, ZnTe and mixtures thereof are very preferred here.

The quantum dots and quantum rods may contain further ligands which are bonded to the surface of the particles. Suitable ligands for this purpose are well known in the prior art and are disclosed, for example, in U.S. Ser. No. 10/656,910 and U.S. 60/578,236. This enables various properties of the quantum dots and quantum rods to be improved. This enables the solubility in certain solvents, matrix materials and polymers to be improved. Further preferred ligands are disclosed in US 2007/0034833A1 and US 20050109989A1.

The terms quantum dot and quantum rod used herein stand for nanoparticles which essentially have a monodisperse size distribution. The dimension of the particles is 500 nm or less down to a dimension of about 1 nm.

Monodisperse means that the particles have a size distribution of ±10% of the said dimension of the particles.

Typical structures and processes for the production of quantum rods are disclosed in US 2013/0135558 A1.

The formulations according to the invention can be used for the production of layers in electronic devices, where the layers produced by means of the formulation according to the invention are applied from solution.

In the production of organic electronic devices, such as, for example, OLEDs, a distinction is made between two basically different processes. In the first process, the relevant compounds are applied by vacuum vapour deposition. This process is very complex and expensive. In the second process, the relevant compounds are applied from solution.

Certain electronic devices are built up from multilayered systems. In the production of multilayered systems of this type, both the above-mentioned processes can be employed. Frequently, individual layers are applied by vapour deposition, while other layers are processed from solution.

The present invention therefore furthermore relates to a process for the production of an organic electronic device, characterised in that at least one layer of the electronic device is produced from solution with the aid of the formulation according to the invention.

Typical processes for the production of layers from solution are, for example, spin coating, or any desired printing process, such as, for example, screen printing, flexographic printing, offset printing or nozzle printing, but particularly preferably LITI (light induced thermal imaging, thermal transfer printing) or ink-jet printing. Formulations are necessary for this purpose.

The organic electronic device is preferably an organic integrated circuit (OIC), an organic field-effect transistor (OFET), an organic thin-film transistor (OTFT), an organic electroluminescent device, an organic solar cell (OSC), an organic optical detector, an organic photoreceptor, but preferably an organic electroluminescent device.

Very preferred organic electroluminescent devices are organic light-emitting transistors (OLETs), organic field-quench devices (OFQDs), organic light-emitting electrochemical cells (OLECs, LECs, LEECs), organic laser diodes (O-lasers) and organic light-emitting diodes (OLEDs), preferably OLECs and OLEDs, very preferably OLEDs.

The formulations can be prepared with the aid of processes which are highly familiar to the person skilled in the art. Typically, the individual components of the formulation are mixed and stirred, if necessary also with supply of heat. The formulation is frequently also degassed or prepared using solvents supersaturated with inert gases. Overall, it must be ensured that only solvents and other components of very high purity are used in order to prevent contamination of the electronic devices with harmful compounds. In particular, it must be ensured that the water, oxygen and halogen content in the formulation is kept low, since, in particular, the performance data of organic electroluminescent devices can be greatly impaired by their presence.

The formulations according to the invention are distinguished by one or more of the following surprising advantages over the prior art:

1. Organic electronic devices, in particular organic electroluminescent devices, produced with the aid of the formulations according to the invention have very good stabilities. In particular, the number of failures can be reduced significantly with the aid of the formulations compared with electronic devices produced with the aid of vacuum evaporation.
2. Organic electronic devices, in particular organic electroluminescent devices, produced with the aid of the formulations according to the invention have comparable efficiencies and voltages compared with devices from the prior art.

3. Organic electronic devices, in particular organic electroluminescent devices, produced with the aid of the formulations according to the invention can be produced easily and inexpensively and are therefore particularly suitable for the mass production of commercial products.
4. With the aid of the formulations according to the invention, layers of organic electronic devices can be produced in a very simple and inexpensive manner, in particular in organic electroluminescent devices which comprise a plurality of components (for example a plurality of matrix compounds).
5. With the aid of the formulations according to the invention, the production processes can be adapted very easily to new requirements.

It should be pointed out that variations of the embodiments described in the present invention fall within the scope of this invention. Each feature disclosed in the present invention can, unless this is explicitly excluded, be replaced by alternative features which serve the same, an equivalent or a similar purpose. Thus, each feature disclosed in the present invention is, unless stated otherwise, to be regarded as an example of a generic series or as an equivalent or similar feature.

All features of the present invention can be combined with one another in any way, unless certain features and/or steps are mutually exclusive. This applies, in particular, to preferred features of the present invention. Equally, features of non-essential combinations can be used separately (and not in combination).

It should furthermore be pointed out that many of the features, and in particular those of the preferred embodiments of the present invention, are themselves inventive and are not merely to be regarded as part of the embodiments of the present invention. For these features, independent protection may be sought additionally or alternatively to each invention presently claimed.

The teaching regarding technical action disclosed with the present invention can be abstracted and combined with other examples.

The invention is explained in greater detail by the following examples without wishing to restrict it thereby.

The person skilled in the art will be able to use the descriptions to produce further electronic devices according to the invention without inventive step and thus carry out the invention throughout the range claimed.

The invention is explained in greater detail by the following examples, without wishing to restrict it thereby. The person skilled in the art will be able use the descriptions to carry out the invention throughout the range disclosed and produce further organic electroluminescent devices according to the invention without inventive step.

EXAMPLES

Example 1

Determination Methods

Determination of HOMO, LUMO, Singlet Level and Triplet Level

The energy levels of the molecular orbitals and the energy of the lowest triplet state $T_1$ or the lowest excited singlet state $S_1$ of the materials are determined via quantum-chemical calculations. To this end, the "Gaussian-09, Revision D.01" software package (Gaussian Inc.) is used in the present application. For the calculation of organic substances without metals (denoted by "org." method), firstly a geometry optimisation is carried out using the semi-empirical method AM1 (Gaussian input line "# AM1 opt") with charge 0 and multiplicity 1. This is followed by an energy calculation (single point) for the electronic ground state and triplet level on the basis of the optimised geometry. The TDDFT (time dependent density functional theory) method B3PW91 with the 6-31G(d) base set (Gaussian input line "# B3PW91/6-31G(d) td=(50-50,nstates=4)") is used here (charge 0, multiplicity 1). For organometallic compounds (denoted by "org.-m" method), the geometry is optimised using the Hartree-Fock method and the LanL2 MB base set (Gaussian input line "# HF/LanL2 MB opt") (charge 0, multiplicity 1). The energy calculation is carried out, as described above, analogously to that of the organic substances, with the difference that the "LanL2DZ" base set is used for the metal atom and the "6-31 G(d)" base set is used for the ligands (Gaussian input line "# B3PW91/gen pseudo=lanl2 td=(50-50,nstates=4)"), The energy calculation gives, for example, the HOMO as the last orbital occupied by two electrons (Alpha occ. eigenvalues) and LUMO as the first unoccupied orbital (alpha virt. eigenvalues) in hartree units, where HEh and LEh stand for the HOMO energy in hartree units and the LUMO energy in hartree units respectively. The energies of the other energy levels, such as HOMO−1, HOMO−2, . . . LUMO+1, LUMO+2 etc., in hartree units are obtained analogously.

For the purposes of this application, the values calibrated with reference to CV measurements ((HEh*27.212)−0.9899)/1.1206) in eV are regarded as the energy levels of the occupied orbitals.

For the purposes of this application, the values calibrated with reference to CV measurements ((LEh*27.212)−2.0041)/1.385) in eV are regarded as the energy levels of the unoccupied orbitals.

The lowest triplet state $T_1$ of a material is defined as the relative excitation energy (in eV) of the triplet state having the lowest energy which arises from the quantum-chemical energy calculation.

The lowest excited singlet state $S_1$ is defined as the relative excitation energy (in eV) of the singlet state having the second lowest energy which arises from the quantum-chemical energy calculation.

The method described herein is independent of the software package used and always gives the same results. Examples of frequently used programmes for this purpose are "Gaussian09W" (Gaussian Inc.) and Q-Chem 4.1 (Q-Chem, Inc.). In the present application, the "Gaussian09W" software package is used for the calculation of the energies.

Table 2 shows the HOMO and LUMO energy levels and $S_1$ and $T_1$ of the various materials.

Determination of Molecular Orbital Overlaps

The overlap of the molecular orbitals which are involved in certain electronic transitions (charge-transfer states) is described with the aid of the parameter Λ. The meaning of the parameter Λ is well known to the person skilled in the art. Determination of the parameter by means of methods which are described in the prior art presents the person skilled in the art with absolutely no difficulties. For the purposes of the present invention, the parameter Λ is determined from the PBHT method in accordance with D. J. Tozer et al. (J. Chem. Phys. 128, 044118 (2008)), which is implemented, for example, in the Q-Chem 4.1 software package from Q-Chem, Inc. The molecular orbitals are calculated here by the method described above. The spatial overlaps for all possible pairs of occupied molecular orbitals, $\varphi_i$, and unoccupied (virtual) molecular orbitals, $\varphi_a$, are subsequently determined from the following equation:

$$O_{ia}=\langle|\varphi_i||\varphi_a|\rangle$$

where the absolute values of the orbitals are used for the calculation. The parameter Λ then arises from the weighted sum over all pairs ia of occupied and unoccupied molecular orbitals in accordance with $$\Lambda=\frac{\sum_{ia}\kappa_{ia}^2 O_{ia}}{\sum_{ia}\kappa_{ia}^2}$$

where the value of $\kappa_{ia}$ is determined by the method of Tozer et al. from the orbital coefficients in the excitation vectors of the resolved TD (time-dependent) eigenvalue equation and where $0\le\Lambda\le1$.

Determination of the PL Quantum Efficiency (PLQE)

A 50 nm thick film of the emission layers used is applied to a quartz substrate. This film comprises the same materials in the same concentrations as in the emission layer of the corresponding OLED, unless the emission layer comprises one or more further components (for example quantum dots, inorganic semiconductors or organic semiconductors). In this case, the film for measurement of the PLQE comprises all materials apart from the further components, and the mixing ratios of the materials present correspond to those in the emission layer of the OLED. The same production conditions as in the production of the emission layer for the OLEDs are used in the production of the films for measurement of the PLQE. An absorption spectrum of the film is measured in the wavelength range from 350-500 nm. To this end, the reflection spectrum R(λ) and the transmission spectrum T(λ) of the sample are determined at an angle of incidence of 6° (i.e. virtually perpendicular incidence). The absorption spectrum in the sense of this application is defined as $A(\lambda)=1-R(\lambda)-T(\lambda)$.

If A(λ) is less than or equal to 0.3 in the range 350-500 nm, the wavelength belonging to the maximum of the absorption spectrum in the range 350-500 nm is defined as $\lambda_{exc}$. If A(λ) is greater than 0.3 for any wavelength, the greatest wavelength at which A(λ) changes from a value less than 0.3 to a value greater than 0.3 or from a value greater than 0.3 to a value less than 0.3 is defined as $\lambda_{exc}$.

The PLQE is determined using a Hamamatsu C9920-02 measurement system. The principle is based on excitation of the sample by light of defined wavelength and measurement of the absorbed and emitted radiation. The sample is located in an Ulbricht sphere ("integrating sphere") during measurement. The spectrum of the excitation light is approximately Gaussian with a full width at half maximum of less than 10 nm and a peak wavelength $\lambda_{exc}$ as defined above.

The PLQE is determined by the evaluation method which is usual for the said measurement system. It is vital to ensure that the sample does not come into contact with oxygen at any time, since the PLQE of materials having a small energetic separation between $S_1$ and $T_1$ is reduced very considerably by oxygen (H. Uoyama et al., Nature 2012, Vol. 492, 234). The measurement is carried out at room temperature.

Determination of the Decay Time

The decay time is determined using a sample produced as described above under "Determination of the PL quantum efficiency (PLQE)". The sample is excited at room temperature by a laser pulse (wavelength 266 nm, pulse duration 1.5 ns, pulse energy 200 μJ, beam diameter 4 mm). The sample is located in a vacuum (less than $10^{-5}$ mbar) here. After the excitation (defined as t=0), the change in the intensity of the emitted photoluminescence over time is measured. The photoluminescence exhibits a steep drop at the beginning, which is attributable to the prompt fluorescence of the TADF compound. As time continues, a slower drop is observed, the delayed fluorescence (see, for example, H. Uoyama et al., Nature, vol. 492, no. 7428, 234-238, 2012 and K. Masui et al., Organic Electronics, vol. 14, no. 11, pp. 2721-2726, 2013). The decay time $t_a$ in the sense of this application is the decay time of the delayed fluorescence and is determined as follows: a time $t_d$ is selected at which the prompt fluorescence has decayed significantly below the intensity of the delayed fluorescence, so that the following determination of the decay time is not influenced by the prompt fluorescence. This choice can be made by a person skilled in the art and belongs to his general expert knowledge. For the measurement data from time $t_d$, the decay time $t_a=t_e-t_d$ is determined, $t_e$ here is the time after $t=t_d$ at which the intensity has for the first time dropped to 1/e of its value at $t=t_d$.

Example 2

Device Examples

The materials required for the following examples are shown in Table 1. The associated HOMO and LUMO energy levels as well as $S_1$ and $T_1$ are indicated in Table 2.

Vacuum-Processed OLEDs

Glass plates coated with structured ITO (indium tin oxide) in a thickness of 50 nm are wet-cleaned (laboratory dishwasher, Merck Extran detergent), subsequently dried by heating at 250° C. in a nitrogen atmosphere for 15 min and treated with an oxygen plasma for 130 s before the coating. These plasma-treated glass plates form the substrates to which the OLEDs are applied. The substrates remain in the vacuum before the coating. The coating begins at the latest 10 min after the plasma treatment.

The materials are applied by thermal vapour deposition in a vacuum chamber. The emission layer here always consists of at least one matrix material (host material) and the emitting material. This is admixed with the matrix material or matrix materials in a certain proportion by volume by coevaporation. An expression such as IC1(60%):WB1(30%):D1(10%) here means that material IC1 is present in the layer in a proportion by volume of 60%, WB1 is present in the layer in a proportion of 30% and D1 is present in the layer in a proportion of 10%. Analogously, the electron-transport layer may also consist of a mixture of two materials.

For characterisation of the OLEDs, current/voltage/luminous density characteristic lines are measured. The luminous density is determined using a calibrated photodiode. Furthermore, the electroluminescence spectrum is measured at a luminous density of 1000 cd/m². The external quantum efficiency (EQE, measured in percent) is calculated therefrom assuming Lambert emission characteristics.

Example V1 in Accordance with the Prior Art

The layer sequence 40 nm of BPA1, then 60 nm of IC1(60%):WB1(30%):D1(10%), then 10 nm of ST1, then 40 nm of ST1(50%):LiQ(50%) and finally 100 nm of aluminium as cathode is applied to the prepared substrates by thermal evaporation.

The emission layer exhibits a PLQE of 84% ($\lambda_{exc}$=350 nm) and a decay time of 4.9 µs ($t_d$=6 µs).

The OLEDs exhibit green emission, 15.1% EQE at 1000 cd/m$^2$ and require a voltage of 7.2 V for this luminous density. 64 components are produced from this example. On operation at 20 mA/cm$^2$ over a period of 200 h, seven of the components fail, i.e. they no longer exhibit any emission at all.

Example V2 in Accordance with the Prior Art

The layer sequence 40 nm of BPA1, then 60 nm of IC1(30%):WB1(60%):D1(10%), then 10 nm of ST1, then 40 nm of ST1(50%):LiQ(50%) and finally 100 nm of aluminium as cathode is applied to the prepared substrates by thermal evaporation.

The emission layer exhibits a PLQE of 79% ($\lambda_{exc}$=350 nm) and a decay time of 5.1 µs ($t_d$=7 µs).

The OLEDs exhibit green emission, 13.9% EQE at 1000 cd/m$^2$ and require a voltage of 6.8 V for this luminous density. 64 components are produced from this example. On operation at 20 mA/cm$^2$ over a period of 200 h, five of the components fail, i.e. they no longer exhibit any emission at all.

OLEDs Having a Solution-Processed Emission Layer

Layers applied by a solution-based method and by a vacuum-based method are combined within an OLED in the example discussed below, so that the processing up to and including the emission layer is carried out from solution and in the subsequent layers by thermal vacuum evaporation.

Cleaned glass plates (cleaning in Miele laboratory dishwasher, detergent Merck Extran) which have been coated with structured ITO (indium tin oxide) in a thickness of 50 nm are treated with a UV ozone plasma for 20 min and subsequently coated with 20 nm of PEDOT:PSS (poly(3,4-ethyl-enedioxythiophene) poly(styrenesulfonate), purchased as CLEVIOS™ P VP Al 4083 from Heraeus Precious Metals GmbH, Germany, applied by spin coating from aqueous solution). These substrates are subsequently dried by heating at 180° C. for 10 min.

A hole-transport layer with a thickness of 20 nm is applied to these substrates. It consists of a polymer of the following structural formula:

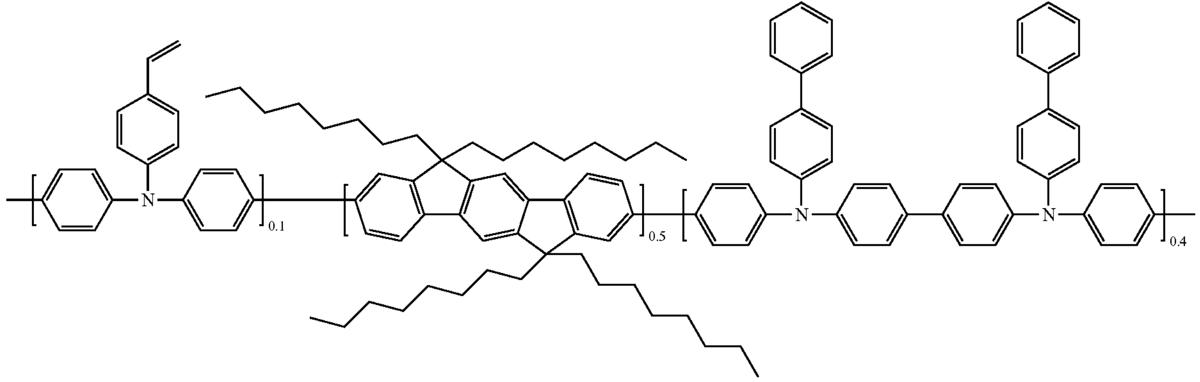

which has been synthesised in accordance with WO 2010/097155. The material is dissolved in toluene. The solids content of the solution is 5 g/l. A layer with a thickness of 20 nm is applied therefrom by spin coating in a nitrogen atmosphere. The sample is subsequently dried by heating at 180° C. in a nitrogen atmosphere for 60 minutes.

The emission layer is subsequently applied. This is always composed of at least one matrix material (host material) and an emitting dopant (emitter). An expression such as IC2 (60%):WB1(30%):D1(10%) means that material IC2 is present in the solution from which the emission layer is produced in a proportion by weight of 60%, WB1 is present in a proportion by weight of 30% and D1 is present in a proportion by weight of 10%. A corresponding solid mixture for the emission layer is dissolved in toluene. The solids content is 18 g/l. The emission layer is applied by spin coating in a nitrogen atmosphere and dried by heating at 180° C. in a nitrogen atmosphere for 10 minutes.

The samples are subsequently introduced into a vacuum chamber without contact with air, and further layers are applied by thermal evaporation. If a layer of this type consists of a plurality of materials, the nomenclature described above for layers applied by thermal vapour deposition applies to the mixing ratios of the individual components.

The OLEDs are characterised as described for the vacuum-processed OLEDs.

Example E1 According to the Invention

For the emission layer, a solid mixture IC2(60%):WB1 (30%):D1(10%) is used. An emission layer with a thickness of 60 nm is produced therefrom as described above. A layer of material ST1 with a thickness of 10 nm and then a layer of ST1(50%):LiQ(50%) with a thickness of 40 nm is subsequently applied by thermal vacuum evaporation. An aluminium layer with a thickness of 100 nm is subsequently applied as cathode by vacuum evaporation.

The emission layer exhibits a PLQE of 82% ($\lambda_{exc}$=350 nm) and a decay time of 4.6 µs ($t_d$=5 µs).

The OLEDs exhibit green emission, 14.2% EQE at 1000 cd/m$^2$ and require a voltage of 7.4 V for this luminous density. 64 components are produced from this example. On operation at 20 mA/cm$^2$ over a period of 200 h, two of the components fail, i.e. they no longer exhibit any emission at all.

Example E2 According to the Invention

The OLED corresponds to Example E1, with the difference that the mixture IC2(60%):WB1(30%):D1(10%) is replaced by the mixture IC2(30%):WB1(60%):D1(10%).

The emission layer exhibits a PLQE of 75% ($\lambda_{exc}$=350 nm) and a decay time of 4.7 μs ($t_d$=5 μs).

The OLEDs exhibit green emission, 12.9% EQE at 1000 cd/m$^2$ and require a voltage of 6.9 V for this luminous density. 64 components are produced from this example. On operation at 20 mA/cm$^2$ over a period of 200 h, none of the components fails.

Example V3 (in Accordance with the Prior Art) Having a Vacuum-Processed Emission Layer The OLED corresponds to that of Example E1, with the difference that the emission layer is vacuum-processed, i.e. the emission layer IC2(60%):WB1(30%):D1(10%) with a thickness of 60 nm is produced by vacuum evaporation.

The emission layer exhibits a PLQE of 86% ($\lambda_{exc}$=350 nm) and a decay time of 4.7 μs ($t_d$=5 μs).

The OLEDs exhibit green emission, 13.5% EQE at 1000 cd/m$^2$ and require a voltage of 7.5 V for this luminous density. 64 components are produced from this example. On operation at 20 mA/cm$^2$ over a period of 200 h, four of the components fail, i.e. they no longer exhibit any emission at all.

Comparison of the Examples

In Examples V1, V2 in accordance with the prior art and Examples E1, E2 according to the invention, very similar materials are employed which are adapted for the respective processing type. In particular, compound D1 is employed as TADF material in all examples.

The comparison of Examples V1 and E1 or V2 and E2 shows that comparable efficiency and voltage can be achieved with solution-processed emission layers as with vacuum-processed emission layers. However, the failure rate of the vacuum-processed OLEDs in operation is significantly higher.

In Examples V3 and E1, identical materials are used, with the difference that in E1 the emission layer is produced from solution and in V3 the emission layer is produced by vacuum evaporation. The performance data are comparable, but the OLEDs having a solution-processed emission layer exhibit significantly fewer failures.

OLEDs Having Emission Layers Containing Quantum Rods

The OLED corresponds to Example E1, with the difference that the mixture IC2(60%):WB1(30%):D1(10%) is replaced by the mixture IC2(45%):WB1(23%):D1(7%): QRod(25%). QRod here is a red-emitting quantum rod which contains a CdSe core having a diameter of 3.9 nm, the surrounding rod with a length of 35 nm consists of CdS. The capping agent used is octadecylphosphonic acid. The peak wavelength of QRod is 635 nm, the half-value width is 30 nm.

The emission layer without QRod exhibits a PLQE of 81% ($\lambda_{exc}$=350 nm) and a decay time of 4.8 μs ($t_d$=5 μs).

The OLED exhibits yellow emission, i.e. a mixture of the green emission of D1 and the red emission of QRod. The EQE is 8.4% at 1000 cd/m$^2$, a voltage of 9.4 V is required for this luminous density.

TABLE 1

| Structural formulae of the materials for the OLEDs |
| --- |
| 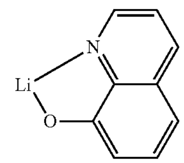  LiQ |
| 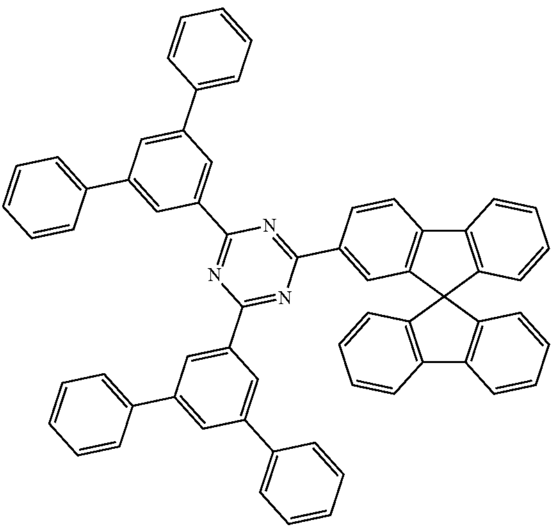 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]  ST1 |
| 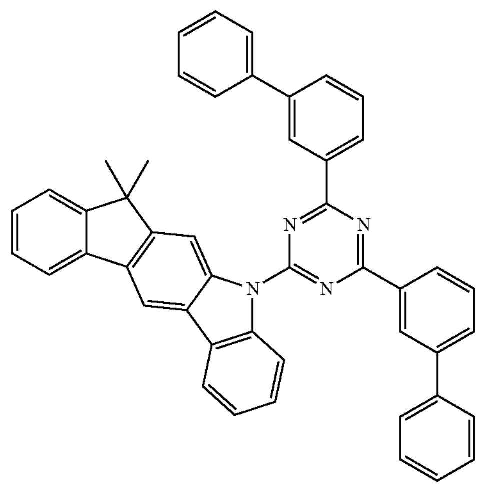 [SMILES: CC1(C)c2ccccc2-c2cc3c4ccccc4n(-c4nc(-c5cccc(-c6ccccc6)c5)nc(-c5cccc(-c6ccccc6)c5)n4)c3cc21]  IC1 |

TABLE 1-continued

Structural formulae of the materials for the OLEDs

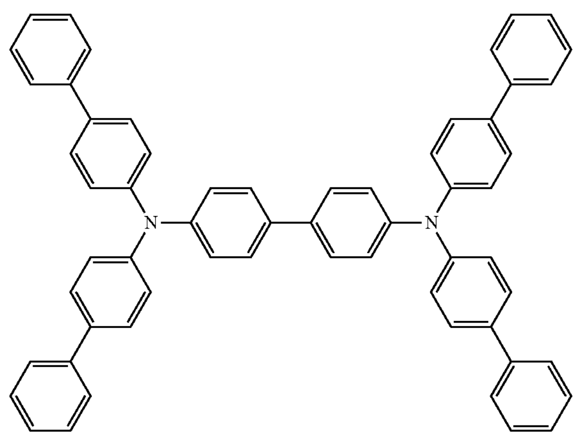 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]

BPA1

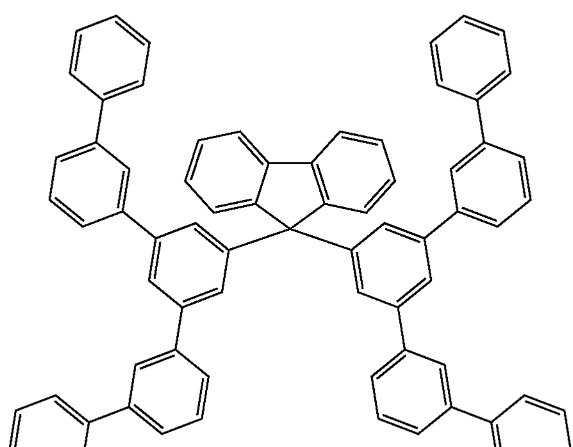
WB1

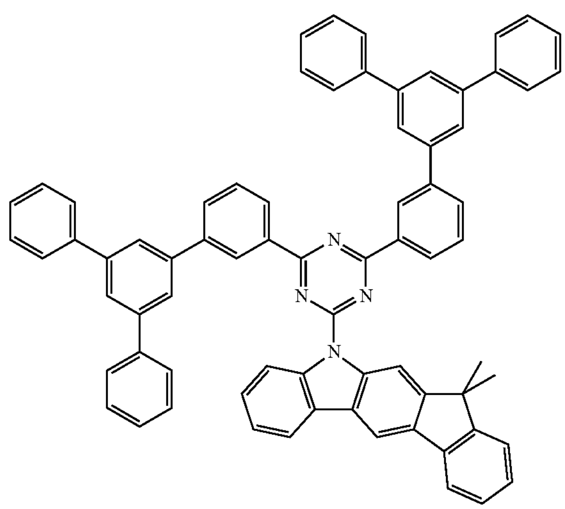 [SMILES: CC1(C)c2ccccc2-c2cc3c4ccccc4n(-c4nc(-c5cccc(-c6cc(-c7ccccc7)cc(-c7ccccc7)c6)c5)nc(-c5cccc(-c6cc(-c7ccccc7)cc(-c7ccccc7)c6)c5)n4)c3cc21]

IC2

TABLE 1-continued

Structural formulae of the materials for the OLEDs

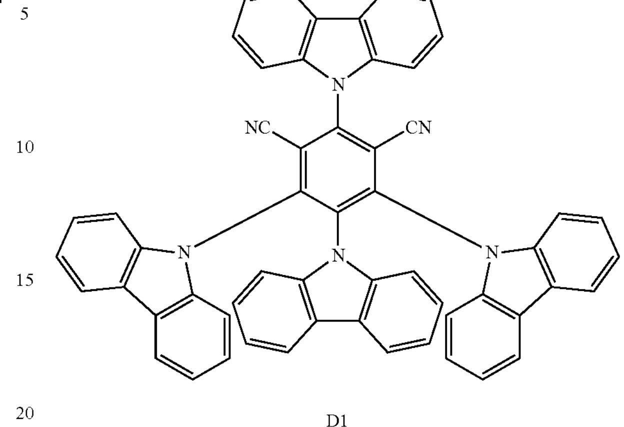

D1

TABLE 2

HOMO, LUMO, $T_1$, $S_1$ of the relevant materials

| Material | Method | HOMO (eV) | LUMO (eV) | $S_1$ (eV) | $T_1$ (eV) |
|---|---|---|---|---|---|
| D1 | org. | −6.11 | −3.40 | 2.50 | 2.41 |
| IC1 | org. | −5.80 | −2.83 | 3.12 | 2.70 |
| IC2 | org. | −5.78 | −2.84 | 3.04 | 2.69 |
| WB1 | org. | −6.16 | −2.24 | 3.38 | 2.95 |
| BPA1 | org. | −5.14 | −2.27 | 3.14 | 2.52 |
| ST1 | org. | −6.03 | −2.82 | 3.32 | 2.68 |
| LiQ | org.-m | −5.17 | −2.39 | 2.85 | 2.13 |

The invention claimed is:

1. A formulation comprising at least one type of organic luminescent compound (TADF compound) and an organic solvent or a mixture of multiple organic solvents, wherein the TADF compound has a separation between the lowest triplet state $T_1$ and the first excited singlet state Si of less than or equal to 0.15 eV;

wherein the formulation comprises a first organic matrix material and a second organic matrix material, wherein the first organic matrix material is an electron-transporting material or a hole-transporting matrix material, and the second organic matrix material is a compound which has a band gap between HOMO and LUMO of greater than or equal to 3.5 eV.

2. The formulation of claim 1, wherein the separation between $S_1$ and $T_1$ of the TADF compound is less than or equal to 0.10 eV.

3. The formulation of claim 1, wherein the TADF compound is an aromatic compound which contains both donor and acceptor substituents.

4. The formulation of claim 1, wherein the surface tension of the solvent or solvents is at least 28 mN/m.

5. The formulation of claim 1, wherein the boiling or sublimation point of the solvent or solvents is less than 300° C.

6. The formulation of claim 1, wherein the viscosity of the solvent or of the individual solvents of a solvent mixture is greater than 3 mPa*s.

7. The formulation of claim 1, wherein the molecular weight of the solvent or of the solvents used in the solvent mixture is less than or equal to 1000 g/mol.

8. The formulation of claim 1, wherein the concentration of the TADF compound in the formulation, based on the entire formulation, is in the range from 1 to 20% by weight.

9. The formulation of claim 1, wherein the solvent is selected from the group consisting of toluene, anisole, o-, m- or p-xylene, methylbenzoate, mesitylene, tetralin, veratrol, THF, methyl-THF, THP, chlorobenzene, dioxane, phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, -terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)-ethane and mixtures thereof.

10. The formulation of claim 1, characterised in that the formulation comprises a matrix material, where the following applies for the lowest unoccupied molecular orbital (LUMO) of the TADF compound LUMO(TADF) and the highest occupied molecular orbital (HOMO) of the matrix HOMO(matrix):

[LUMO(TADF)−HOMO(matrix)] is greater than or equal to [$S_1$(TADF)−0.4 eV], where $S_1$(TADF) is the first excited singlet state $S_1$ of the TADF compound.

11. A method for producing one or more layers of an organic electronic device from solution comprising utilizing the formulation of claim 1.

12. A process for the production of an organic electronic device, comprising producing at least one layer of the electronic device from solution with the aid of the formulation of claim 1.

13. The process of claim 12, characterised in that the electronic device is an organic electroluminescent device.

* * * * *